US009161773B2

(12) United States Patent
Schaller et al.

(10) Patent No.: US 9,161,773 B2
(45) Date of Patent: Oct. 20, 2015

(54) TISSUE REMOVAL TOOLS AND METHODS OF USE

(75) Inventors: Laurent B. Schaller, Los Altos, CA (US); Steven S Golden, Menlo Park, CA (US); Jeffrey L. Emery, Emerald Hills, CA (US); James K Lee, San Mateo, CA (US); Mark Y. Hirotsuka, San Jose, CA (US); Russell J. Borg, Campbell, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 72 days.

(21) Appl. No.: 13/166,615

(22) Filed: Jun. 22, 2011

(65) Prior Publication Data

US 2011/0313529 A1    Dec. 22, 2011

Related U.S. Application Data

(63) Continuation-in-part of application No. 12/640,171, filed on Dec. 17, 2009, now Pat. No. 8,470,043.

(60) Provisional application No. 61/140,401, filed on Dec. 23, 2008.

(51) Int. Cl.
*A61F 2/44* (2006.01)
*A61B 17/32* (2006.01)
*A61B 17/3205* (2006.01)
*A61B 17/00* (2006.01)

(52) U.S. Cl.
CPC ....... *A61B 17/32002* (2013.01); *A61B 17/3205* (2013.01); *A61B 17/32056* (2013.01); *A61B 2017/00261* (2013.01); *A61B 2017/00867* (2013.01); *A61B 2017/320032* (2013.01); *A61B 2017/320052* (2013.01)

(58) Field of Classification Search
CPC .. A61B 17/66; A61B 17/885; A61B 17/8861; A61B 17/8863; A61B 17/025; A61B 17/0256; A61F 2/4611; A61F 2002/4622
USPC .......... 623/17.11–17.17; 606/86 R, 105, 113, 606/114, 159, 170–172, 177–183
See application file for complete search history.

(56) References Cited

U.S. PATENT DOCUMENTS

| | | | |
|---|---|---|---|
| 3,807,390 | A | 4/1974 | Ostrowski et al. |
| 4,846,175 | A | 7/1989 | Frimberger |
| 5,129,889 | A | 7/1992 | Hahn et al. |
| 5,219,358 | A | 6/1993 | Bendel et al. |
| 5,267,994 | A | 12/1993 | Gentelia et al. |
| 5,342,394 | A | 8/1994 | Matsuno et al. |
| 5,345,945 | A | 9/1994 | Hodgson et al. |

(Continued)

FOREIGN PATENT DOCUMENTS

| | | |
|---|---|---|
| DE | 4222121 C1 | 9/1993 |
| EP | 0682910 A1 | 11/1995 |
| WO | WO 98/17190 A3 | 4/1998 |

*Primary Examiner* — Eduardo C Robert
*Assistant Examiner* — Michelle C Eckman
(74) *Attorney, Agent, or Firm* — Cook Alex Ltd.

(57) ABSTRACT

Discectomy or disc preparation system that includes a guide member that is changeable from a deployment configuration for insertion into an intervertebral disc space to a deployed configuration upon being deployed into the intervertebral disc. The system also includes at least one tissue manipulator, such as cutting, scraping and extraction elements, that can be moved or tracked longitudinally along the guide member into and through the intervertebral disc space.

28 Claims, 13 Drawing Sheets

(56) References Cited

U.S. PATENT DOCUMENTS

| | | |
|---|---|---|
| 5,366,490 A | 11/1994 | Edwards et al. |
| 5,383,884 A | 1/1995 | Summers |
| 5,397,304 A | 3/1995 | Truckai |
| 5,423,806 A | 6/1995 | Dale et al. |
| 5,433,739 A | 7/1995 | Sluijter et al. |
| 5,487,757 A | 1/1996 | Truckai et al. |
| 5,500,012 A | 3/1996 | Brucker et al. |
| 5,554,163 A * | 9/1996 | Shturman ............... 606/159 |
| 5,571,147 A | 11/1996 | Sluijter et al. |
| 5,599,346 A | 2/1997 | Edwards et al. |
| 5,697,909 A | 12/1997 | Eggers et al. |
| 5,755,732 A | 5/1998 | Green et al. |
| 5,788,713 A | 8/1998 | Dubach et al. |
| 5,871,501 A | 2/1999 | Leschinsky et al. |
| 5,885,217 A | 3/1999 | Gisselberg et al. |
| 5,916,166 A | 6/1999 | Reiss et al. |
| 5,980,471 A | 11/1999 | Jafari |
| 5,980,504 A | 11/1999 | Sharkey et al. |
| 6,007,570 A | 12/1999 | Sharkey et al. |
| 6,099,514 A | 8/2000 | Sharkey et al. |
| 6,126,682 A | 10/2000 | Sharkey et al. |
| 6,224,630 B1 | 5/2001 | Bao et al. |
| 6,245,107 B1 | 6/2001 | Ferree |
| 6,277,112 B1 | 8/2001 | Underwood et al. |
| 6,375,635 B1 | 4/2002 | Moutafis et al. |
| 6,387,130 B1 | 5/2002 | Stone et al. |
| 6,419,704 B1 | 7/2002 | Ferree |
| 6,468,270 B1 | 10/2002 | Hovda et al. |
| 6,488,710 B2 | 12/2002 | Besselink |
| 6,491,690 B1 | 12/2002 | Goble et al. |
| 6,530,926 B1 | 3/2003 | Davison |
| 6,551,319 B2 | 4/2003 | Lieberman |
| 6,558,386 B1 | 5/2003 | Cragg |
| 6,558,390 B2 | 5/2003 | Cragg |
| 6,562,033 B2 | 5/2003 | Shah et al. |
| 6,592,625 B2 | 7/2003 | Cauthen |
| 6,607,505 B1 * | 8/2003 | Thompson et al. ........ 604/95.04 |
| 6,607,530 B1 | 8/2003 | Carl et al. |
| 6,676,665 B2 | 1/2004 | Foley et al. |
| 6,714,822 B2 | 3/2004 | King et al. |
| 6,726,684 B1 | 4/2004 | Woloszko et al. |
| 6,733,496 B2 * | 5/2004 | Sharkey et al. ................ 606/41 |
| 6,749,605 B2 | 6/2004 | Ashley et al. |
| 6,764,491 B2 | 7/2004 | Frey et al. |
| 6,767,347 B2 | 7/2004 | Sharkey et al. |
| 6,773,432 B1 * | 8/2004 | Clayman et al. ................ 606/41 |
| 6,821,276 B2 | 11/2004 | Lambrecht et al. |
| 6,830,570 B1 | 12/2004 | Frey et al. |
| 6,878,155 B2 | 4/2005 | Sharkey et al. |
| 6,923,811 B1 | 8/2005 | Carl et al. |
| 6,939,351 B2 | 9/2005 | Eckman |
| 6,953,458 B2 | 10/2005 | Loeb |
| 6,964,667 B2 | 11/2005 | Shaolian et al. |
| 6,976,949 B2 | 12/2005 | Winkler et al. |
| 7,004,970 B2 | 2/2006 | Cauthen, III et al. |
| 7,025,765 B2 | 4/2006 | Balbierz et al. |
| 7,052,516 B2 | 5/2006 | Cauthen, III et al. |
| 7,056,321 B2 | 6/2006 | Pagliuca et al. |
| 7,069,087 B2 | 6/2006 | Sharkey et al. |
| 7,114,501 B2 | 10/2006 | Johnson et al. |
| 7,124,761 B2 | 10/2006 | Lambrecht et al. |
| 7,144,397 B2 | 12/2006 | Lambrecht et al. |
| 7,179,225 B2 | 2/2007 | Shluzas et al. |
| 7,211,055 B2 | 5/2007 | Diederich |
| 7,241,297 B2 | 7/2007 | Shaolian et al. |
| 7,282,020 B2 | 10/2007 | Kaplan |
| 7,309,336 B2 | 12/2007 | Ashley et al. |
| 7,318,823 B2 | 1/2008 | Sharps et al. |
| 7,318,826 B2 | 1/2008 | Teitelbaum et al. |
| 7,322,962 B2 | 1/2008 | Forrest |
| 7,331,956 B2 | 2/2008 | Hovda et al. |
| 7,331,963 B2 | 2/2008 | Bryan et al. |
| RE40,156 E | 3/2008 | Sharps et al. |
| 7,963,915 B2 * | 6/2011 | Bleich ..................... 600/184 |
| 8,394,102 B2 * | 3/2013 | Garabedian et al. ........ 606/86 A |
| 2002/0026197 A1 | 2/2002 | Foley et al. |
| 2002/0147444 A1 * | 10/2002 | Shah et al. ........................ 606/28 |
| 2002/0156530 A1 | 10/2002 | Lambrecht et al. |
| 2003/0014047 A1 | 1/2003 | Woloszko et al. |
| 2003/0040796 A1 | 2/2003 | Ferree |
| 2003/0158545 A1 | 8/2003 | Hovda et al. |
| 2003/0204189 A1 | 10/2003 | Cragg |
| 2004/0015218 A1 | 1/2004 | Finch et al. |
| 2004/0024463 A1 | 2/2004 | Thomas, Jr. et al. |
| 2004/0049180 A1 | 3/2004 | Sharps et al. |
| 2004/0059333 A1 | 3/2004 | Carl et al. |
| 2004/0073216 A1 | 4/2004 | Lieberman |
| 2004/0092988 A1 | 5/2004 | Shaolian et al. |
| 2004/0106940 A1 | 6/2004 | Shaolian et al. |
| 2004/0116922 A1 | 6/2004 | Hovda et al. |
| 2004/0127893 A1 | 7/2004 | Hovda |
| 2004/0148028 A1 | 7/2004 | Ferree et al. |
| 2004/0153064 A1 | 8/2004 | Foley et al. |
| 2004/0167625 A1 | 8/2004 | Beyar et al. |
| 2004/0260305 A1 | 12/2004 | Gorensek et al. |
| 2005/0021030 A1 | 1/2005 | Pagliuca et al. |
| 2005/0033292 A1 | 2/2005 | Teitelbaum et al. |
| 2005/0049623 A1 | 3/2005 | Moore et al. |
| 2005/0090833 A1 | 4/2005 | DiPoto |
| 2005/0090899 A1 | 4/2005 | DiPoto |
| 2005/0113832 A1 | 5/2005 | Molz, IV et al. |
| 2005/0131540 A1 | 6/2005 | Trieu |
| 2005/0131541 A1 | 6/2005 | Trieu |
| 2005/0137601 A1 | 6/2005 | Assell et al. |
| 2005/0137605 A1 | 6/2005 | Assell et al. |
| 2005/0149049 A1 | 7/2005 | Assell et al. |
| 2005/0187537 A1 | 8/2005 | Loeb et al. |
| 2005/0203527 A1 | 9/2005 | Carrison et al. |
| 2005/0251134 A1 * | 11/2005 | Woloszko et al. .............. 606/46 |
| 2005/0261684 A1 | 11/2005 | Shaolian et al. |
| 2005/0261692 A1 | 11/2005 | Carrison et al. |
| 2006/0015131 A1 | 1/2006 | Kierce et al. |
| 2006/0025797 A1 | 2/2006 | Lock et al. |
| 2006/0036241 A1 | 2/2006 | Siegal |
| 2006/0041295 A1 | 2/2006 | Osypka |
| 2006/0047178 A1 | 3/2006 | Winkler et al. |
| 2006/0058826 A1 | 3/2006 | Evans et al. |
| 2006/0074425 A1 | 4/2006 | Sutterlin et al. |
| 2006/0149268 A1 | 7/2006 | Truckai et al. |
| 2006/0161162 A1 | 7/2006 | Lambrecht et al. |
| 2006/0178666 A1 | 8/2006 | Cosman et al. |
| 2006/0195091 A1 | 8/2006 | McGraw et al. |
| 2006/0195094 A1 | 8/2006 | McGraw et al. |
| 2006/0206116 A1 | 9/2006 | Yeung |
| 2006/0217811 A1 | 9/2006 | Lambrecht et al. |
| 2006/0224154 A1 | 10/2006 | Shadduck et al. |
| 2006/0229625 A1 | 10/2006 | Truckai et al. |
| 2006/0235418 A1 | 10/2006 | Gil et al. |
| 2006/0241577 A1 | 10/2006 | Balbierz et al. |
| 2006/0247600 A1 | 11/2006 | Yeung et al. |
| 2006/0247784 A1 | 11/2006 | Kim |
| 2006/0265076 A1 | 11/2006 | Carter et al. |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0016273 A1 | 1/2007 | Scarborough et al. |
| 2007/0027545 A1 | 2/2007 | Carls et al. |
| 2007/0055259 A1 | 3/2007 | Norton et al. |
| 2007/0055262 A1 * | 3/2007 | Tomita et al. .................... 606/82 |
| 2007/0060935 A1 | 3/2007 | Schwardt et al. |
| 2007/0067035 A1 | 3/2007 | Falahee |
| 2007/0093822 A1 | 4/2007 | Dutoit et al. |
| 2007/0093899 A1 | 4/2007 | Dutoit et al. |
| 2007/0118219 A1 | 5/2007 | Hyde, Jr. |
| 2007/0123888 A1 | 5/2007 | Bleich et al. |
| 2007/0123986 A1 * | 5/2007 | Schaller ..................... 623/17.11 |
| 2007/0149990 A1 | 6/2007 | Palmer et al. |
| 2007/0162032 A1 | 7/2007 | Johnson et al. |
| 2007/0162062 A1 | 7/2007 | Norton et al. |
| 2007/0162127 A1 | 7/2007 | Peterman et al. |
| 2007/0162135 A1 | 7/2007 | Segal et al. |
| 2007/0168041 A1 | 7/2007 | Kadiyala |
| 2007/0168043 A1 | 7/2007 | Ferree |

(56) References Cited

U.S. PATENT DOCUMENTS

| | | |
|---|---|---|
| 2007/0198021 A1 | 8/2007 | Wales |
| 2007/0198025 A1 | 8/2007 | Trieu et al. |
| 2007/0208426 A1 | 9/2007 | Trieu |
| 2007/0213704 A1 | 9/2007 | Truckai et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0255286 A1 | 11/2007 | Trieu |
| 2007/0255406 A1 | 11/2007 | Trieu |
| 2007/0255703 A1 | 11/2007 | Maruyama et al. |
| 2007/0260252 A1* | 11/2007 | Schmitz et al. ............ 606/79 |
| 2007/0260270 A1 | 11/2007 | Assell et al. |
| 2007/0265652 A1 | 11/2007 | Assell et al. |
| 2007/0265691 A1 | 11/2007 | Swanson |
| 2007/0299521 A1 | 12/2007 | Glenn et al. |
| 2008/0009826 A1 | 1/2008 | Miller et al. |
| 2008/0009828 A1 | 1/2008 | Miller et al. |
| 2008/0009847 A1 | 1/2008 | Ricart et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0021435 A1 | 1/2008 | Miller et al. |
| 2008/0027407 A1 | 1/2008 | Miller et al. |
| 2008/0033465 A1 | 2/2008 | Schmitz et al. |
| 2008/0058707 A1 | 3/2008 | Ashley et al. |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0086157 A1 | 4/2008 | Stad et al. |
| 2009/0012612 A1* | 1/2009 | White et al. ............ 623/11.11 |
| 2009/0143716 A1* | 6/2009 | Lowry et al. ............ 604/22 |
| 2010/0286782 A1* | 11/2010 | Schaller et al. ............ 623/17.12 |
| 2012/0022651 A1* | 1/2012 | Akyuz et al. ............ 623/17.16 |

* cited by examiner

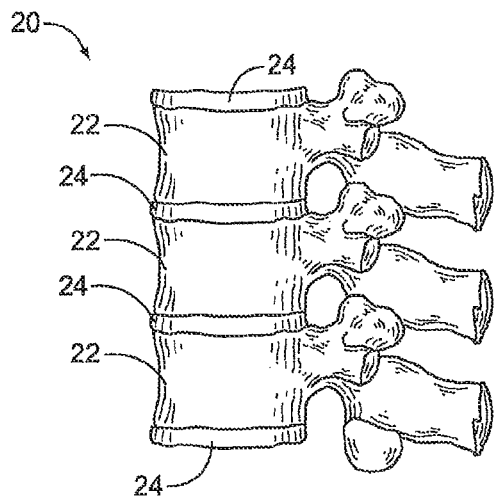
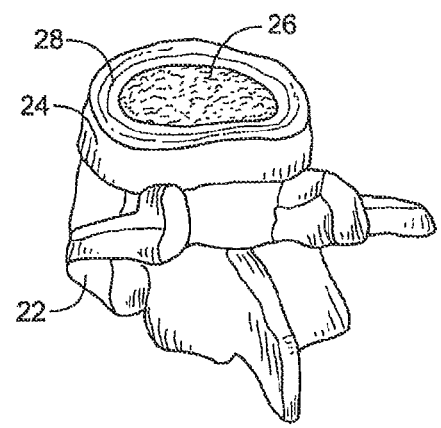
FIG. 1
FIG. 2
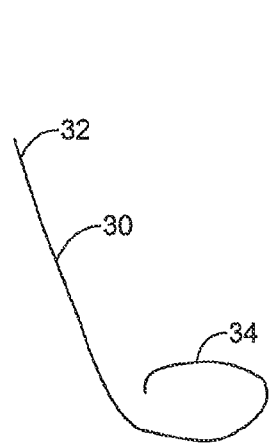
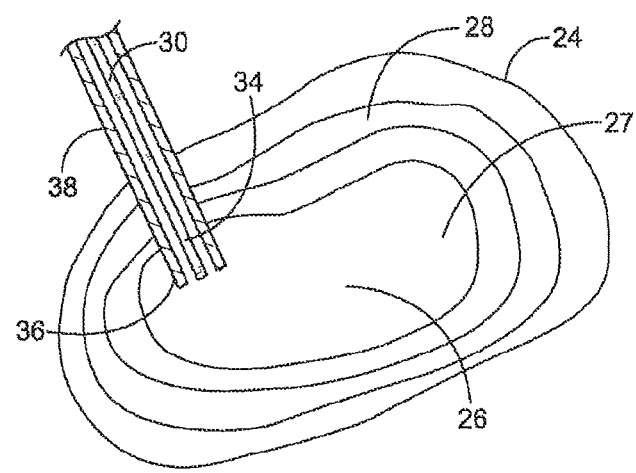
FIG. 3
FIG. 4

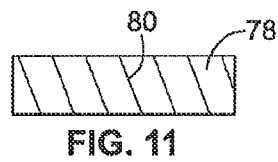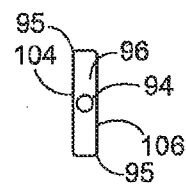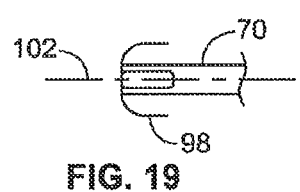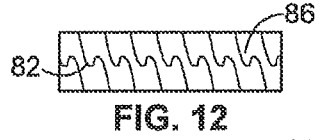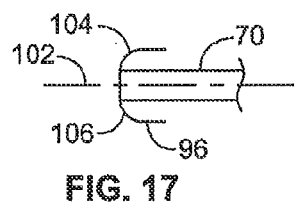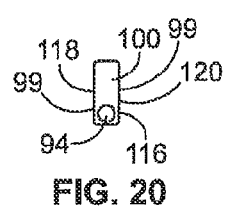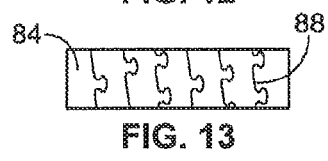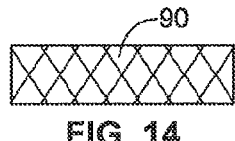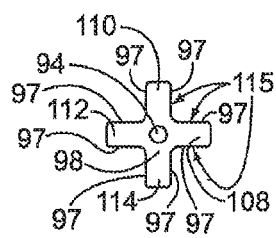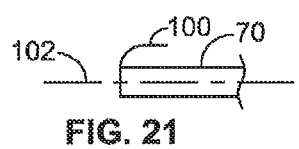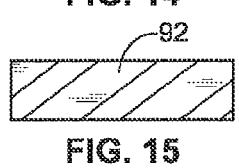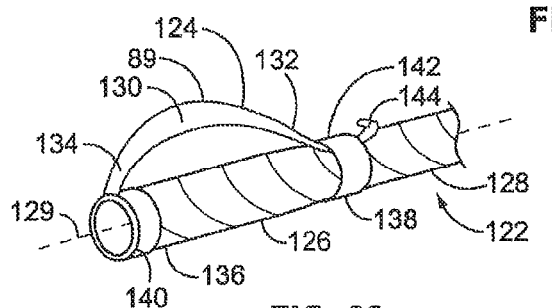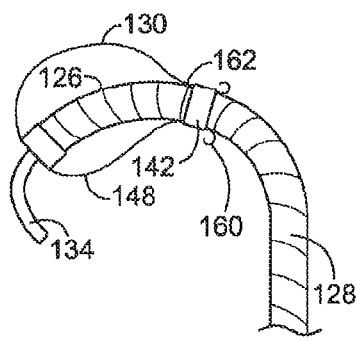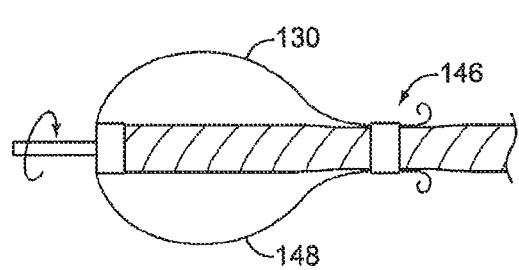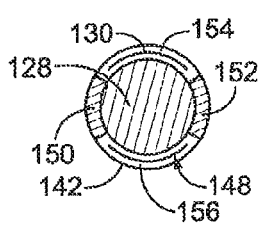

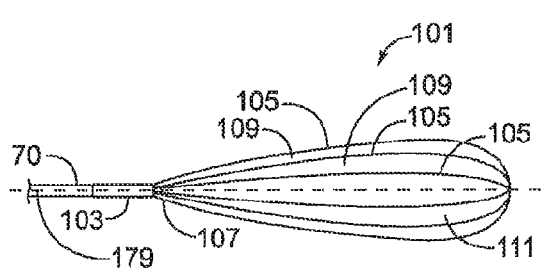
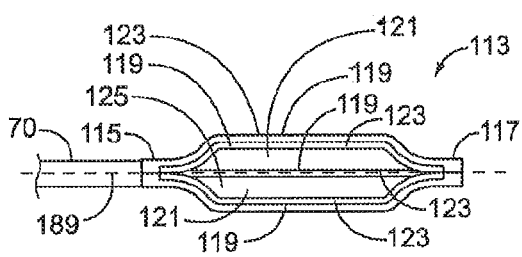
FIG. 31   FIG. 32A
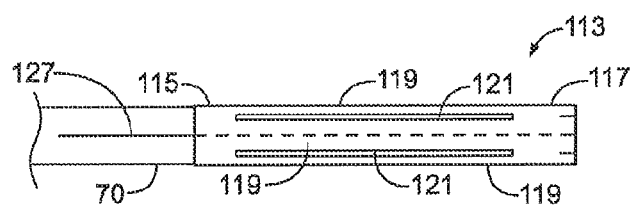
FIG. 32B
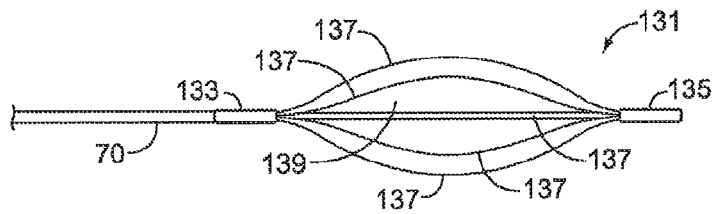
FIG. 33
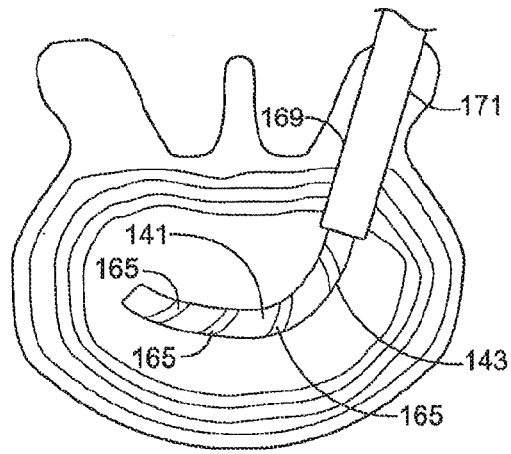
FIG. 34

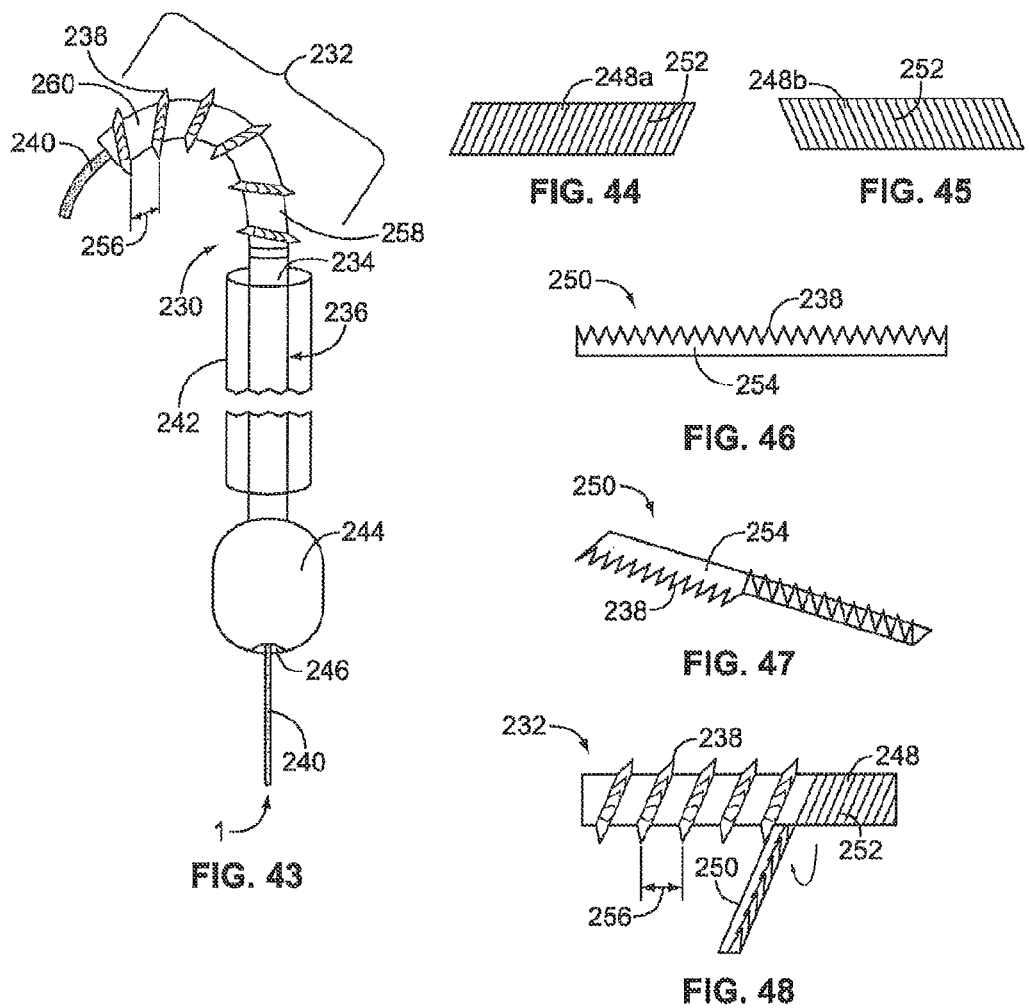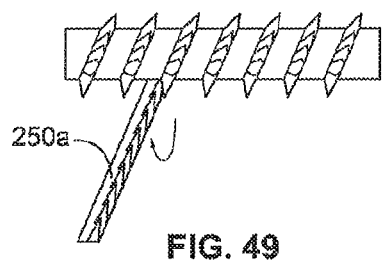

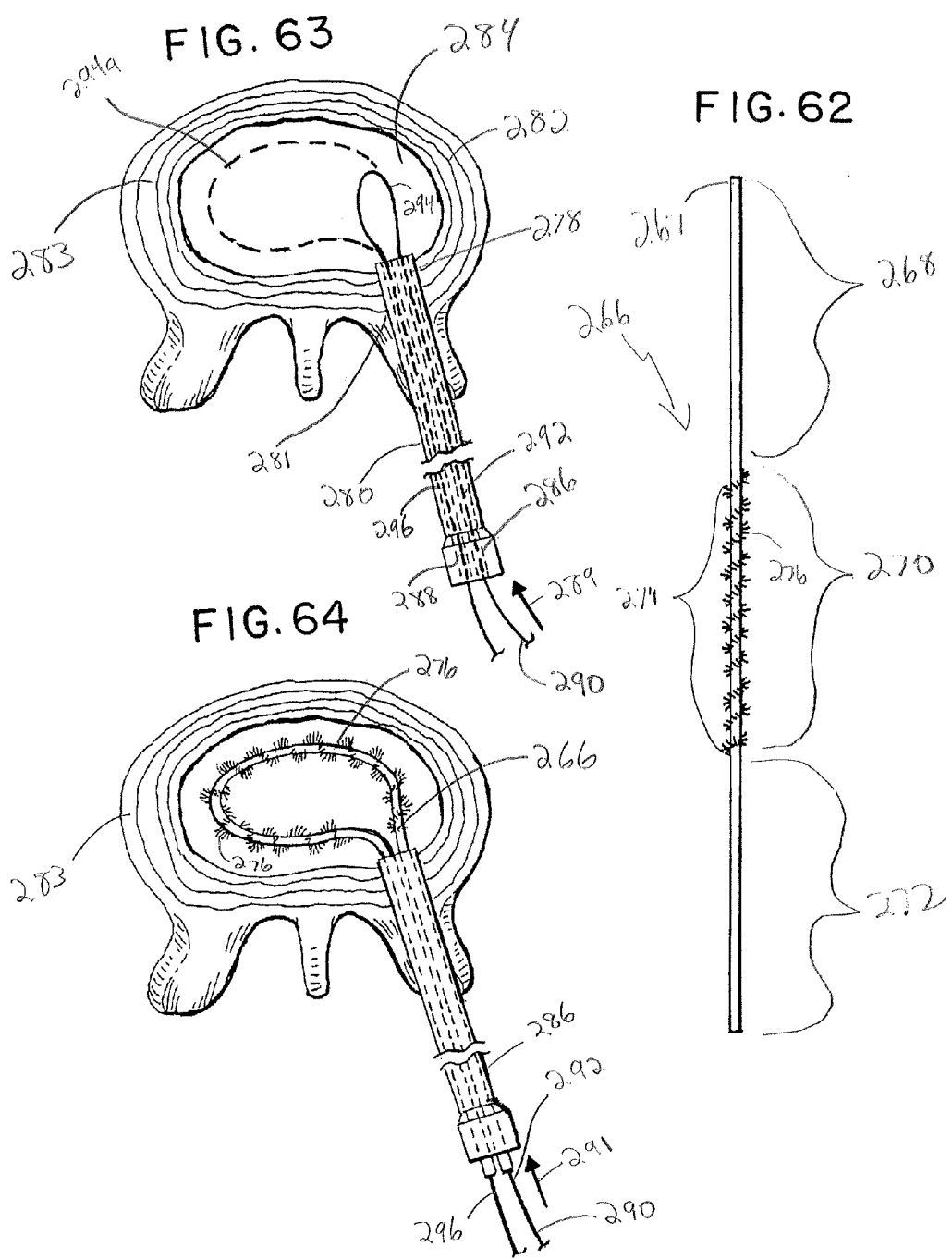

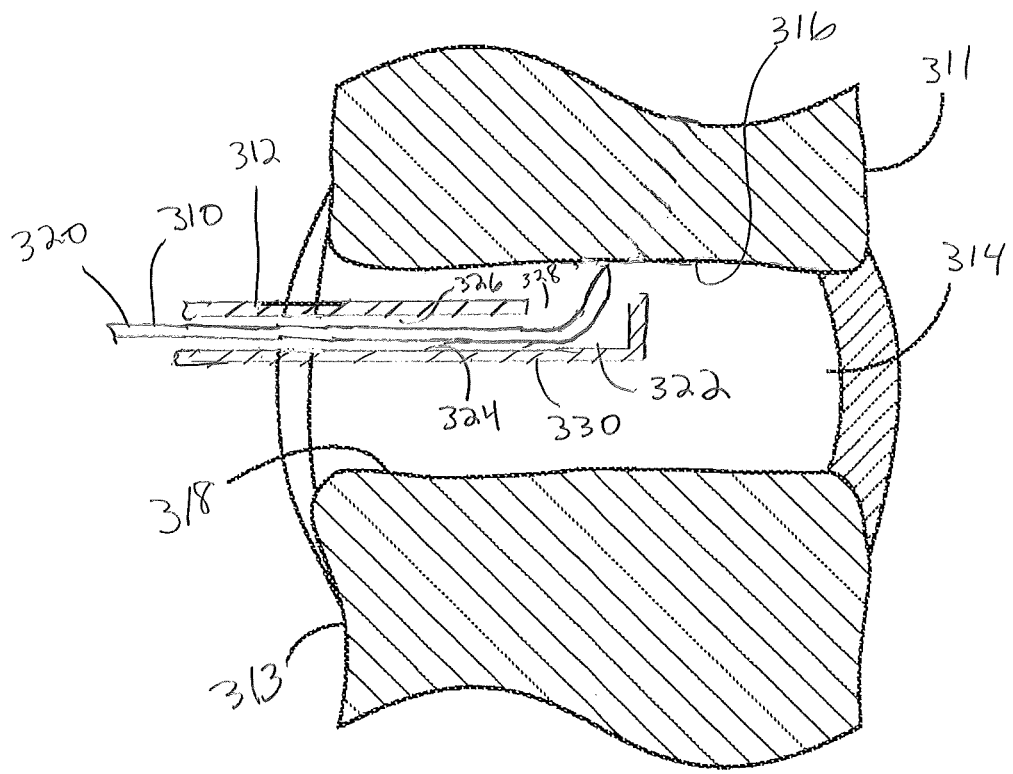

TISSUE REMOVAL TOOLS AND METHODS OF USE

The present application is a continuation-in-part of copending U.S. patent application Ser. No. 12/640,171, which was filed on Dec. 17, 2009 and claims the benefit of U.S. Provisional Application Ser. No. 61/140,401, filed Dec. 23, 2008, both of which are incorporated herein by reference.

FIELD OF THE INVENTION

The present invention generally relates to apparatus and methods employed in minimally invasive surgical procedures to cut and remove tissue from a patient and, more particularly, to apparatus and methods that may be utilized in a minimally invasive, e.g. endoscopic, surgical procedure to cut and remove tissue from an intervertebral disc.

BACKGROUND OF THE INVENTION

A major cause of chronic, and often disabling, back pain is disruption or degeneration of an intervertebral disc. The spine is comprised of bony vertebrae separated by intervertebral discs. Each intervertebral disc connects adjacent vertebrae and forms a joint that allows movement of the vertebral column. An intervertebral disc is generally divided into two regions: the nucleus pulposus and the annulus fibrosus. The nucleus pulposus is a gelatinous-like tissue that lies at the center of the disc and provides a cushion between adjacent vertebrae. The annulus is made up of collagen fibers that form concentric lamellae that surround and contain the nucleus pulposus.

There are many causes of disruption and degeneration of intervertebral discs, which can be broadly categorized as mechanical, genetic and biochemical. Mechanical damage includes herniation in which a portion of the nucleus pulposus projects through a fissure or tear in the annulus fibrosus. Genetic and biochemical causes usually result from changes in the biochemical processes of a disc. Such changes can be attributed to genetic disorders or environmental influences. Degenerative disc condition is commonly caused by a change in the biochemical process of an intervertebral disc. Such degeneration is a progressive process that usually begins with a decrease in the ability of the nucleus pulposus to absorb water. With a loss of water content, the nucleus becomes dehydrated, resulting in a decrease of internal disc hydraulic pressure, and ultimately to a loss of disc height. This loss of disc height can cause the annulus to buckle, eventually resulting in annular fissures and ruptures. Herniation occurs when a rupture leads to protrusion of the nucleus pulposus through the annulus.

Furthermore, disc height plays an important role in the functionality of the intervertebral disc and spinal column, and changes in disc height can have both local and wider effects. On the local (or cellular) level, decreased disc height may result in increased pressure in the nucleus pulposus, which can lead to a decrease in normal cell operation and an increase in cell death and disintegration. In addition, increases in intradiscal pressure may create an unfavorable environment for fluid transfer into the disc, which can cause a further decrease in disc height.

Decreased disc height also results in significant changes in the larger mechanical stability of the spine. With decreasing height of the disc, the facet joints bear increasing loads and may undergo hypertrophy and degeneration. Decreased stiffness of the spinal column and increased range of motion resulting from loss of disc height can lead to further instability of the spine, as well as back pain.

Several disc defects may be treated by implantation of a prosthetic into the nuclear space of the intervertebral disc. Some procedures that may include insertion of a prosthetic into the disc are spinal fusion and disc repair and replacement. Prior to implantation of most prosthesis, a discectomy is often performed to prepare the nuclear space for implantation of the prosthetic and, when spinal fusion is desired, to facilitate bony fusion between the vertebral bodies. Some implantation procedures may require a total discectomy in which the majority (and usually all) of the volume of the nucleus pulposus is removed. Others may require a partial discectomy in which only a portion of the nucleus pulposus is removed.

Traditionally, discectomy procedures are performed with the use of simple manual instruments, such as curettes, which are cupped scrapers with a variety of end configurations, pituitary rongeurs, which are jaw like gripping or cutting members, and rasps, which include a rough surface that is employed to roughen and scrape endplate tissue of adjacent vertebrae. For a typical posterior surgical approach, an incision is made through the back of a patient and access to the disc space is achieved. The manual instruments are then inserted through the access to the intervertebral disc requiring treatment. The curettes and rongeurs are used to cut, tear, and remove nucleus pulposus tissue one piece at a time, and the rasps are utilized to roughen or scrape the endplates of adjacent vertebrae.

There are some significant limitations associated with performing a discectomy with these manual instruments. For example, since the disc tissue is cut and removed a piece at a time, dozens of repeated cycles of insertion and removal of the traditional instruments are required to remove the desired amount of tissue. The repeated cycles increase the risk of associated nerve damage and the amount of trauma to the surrounding tissue. Additionally, guidance of the traditional instruments is largely controlled by the dexterity of the surgeon, and even with the most skilled surgeons, repeated precise placement of such instruments is a challenge. Furthermore, because of the geometric configuration of traditional instruments and the limited work space associated with intervertebral disc procedures, it can be difficult to adequately remove the required amount of material from the nuclear space. This is particularly the case with a unilateral (one of the more preferred) access of the disc space, where the contralateral half of the disc is significantly more difficult to reach. Finally, surgeons typically use traditional instruments without being able to see the tissue being removed. Thus, the surgeon must be able to distinguish nucleus tissue from annulus tissue and bone tissue by "feel." Thus, if the surgeon has a difficult time distinguishing between these tissues, serious damage can be done to the annulus of the disc or the vertebral bodies.

Other methods and techniques have been developed for performing discectomy procedures. However, these methods and techniques also have limitations and risks associated with their use. Accordingly, there remains a need for improved discectomy devices and methods.

SUMMARY

The present disclosure is directed to tissue manipulation systems and tools that can be used to disrupt tissue of a patient, such as by cutting and/or scraping. The tissue manipulation system and tools also may be used to remove tissue from a patient. The tools disclosed herein are particularly useful for performing discectomy procedures and preparing the nuclear space for prosthetic implantation and spinal fusion. The tools described herein may be used individually for their intended purpose or together in the system.

In one aspect, the present disclosure provides a tissue manipulation system for manipulating tissue in or adjacent an intervertebral disc, the system comprising a deployment cannula having a proximal end portion, a distal end portion and at least one internal lumen. The system also includes a guide member that is movable within the internal lumen of the cannula and out of the distal end portion of the cannula. When the guide member is advanced out of the distal end portion of the cannula, the distal end portion of the guide member defines a continuous loop extending from and returning into the lumen of the cannula. The system further includes a tissue manipulator movable within the internal lumen of the cannula. The tissue manipulator has a passageway for receiving the guide member such that the tissue manipulator is advanceable over the guide member, out of the distal end portion of the cannula and over the continuous loop defined by the guide member.

In another aspect, a tissue manipulation system for manipulating tissue in or adjacent to an intervertebral disc, the system comprises an elongated guide member including a distal end portion adapted for insertion into the intervertebral disc. The distal end portion of the guide member forms a substantially looped configuration within the disc. The system also includes a tissue manipulator having a passageway for receiving the guide member such that the tissue manipulator is advanceable over the substantially looped configuration of the distal end portion of the guide member.

In yet another aspect, a method of manipulating tissue of or adjacent to an intervertebral disc comprises inserting a guide member into an intervertebral disc. A distal end portion of the guide member is then formed into a substantially continuous loop. At least one tissue manipulator is advanced along the substantially continuous loop to manipulate tissue within and/or adjacent to the disc.

These and other aspects of the present disclosure are set forth in the following detailed description. In that respect, it should be noted that the present invention includes a number of different aspects which may have utility alone and/or in combination with other aspects. Accordingly, the above summary is not an exhaustive identification of each such aspect that is now or may hereafter be claimed, but represents an overview of the present invention to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein:

FIG. 1 is a side view of a healthy vertebral (spinal) column;

FIG. 2 is a perspective view of an intervertebral disc and its associated inferior vertebra;

FIG. 3 is a top view of one embodiment of a guide member constructed in accordance with the present disclosure;

FIG. 4 is a cross-sectional view of an intervertebral disc having a deployment cannula inserted through the annulus fibrosus and partially into the nuclear space;

FIG. 11-15 are partial side views of different embodiments of pushing members constructed in accordance with the present disclosure;

FIG. 16 is a front end view of one embodiment of a tissue manipulation element constructed in accordance with the present disclosure;

FIG. 17 is a side view of the tissue manipulation element of FIG. 16;

FIG. 18 is a front view of another embodiment of a tissue manipulation element constructed in accordance with the present disclosure;

FIG. 19 is a side view of the tissue manipulation element of FIG. 18;

FIG. 20 is a front view of yet another embodiment of a tissue manipulation element constructed in accordance with the present disclosure;

FIG. 21 is a side view of the tissue manipulation element of FIG. 20;

FIG. 22 is a perspective view of another embodiment of a tissue manipulation element constructed in accordance with the present disclosure;

FIG. 23 is a side view of a further embodiment of a tissue manipulation element constructed in accordance with the present disclosure;

FIG. 24 is a top view of the tissue manipulation element of FIG. 23;

FIG. 25 is a cross-sectional view of the tissue manipulation element of FIG. 23;

FIG. 31 is a side view of another embodiment of a tissue manipulation element constructed in accordance with the present disclosure;

FIG. 32A is a side view of yet another embodiment of a tissue manipulation element constructed in accordance with the present disclosure;

FIG. 32B is a side view of the tissue manipulation element of FIG. 32A shown in a deployment configuration;

FIG. 33 is a side view of yet another embodiment of a tissue manipulation element constructed in accordance with the present disclosure;

FIG. 34 is a top view of one embodiment of a guide member constructed in accordance with the present disclosure and shown deployed within a disc space;

FIG. 43 is a side view of one embodiment of a tissue manipulation tool constructed in accordance with the present disclosure;

FIG. 44 is a side elevation view of one embodiment of an internal support member;

FIG. 45 is a side elevation view of another embodiment of an internal support member;

FIG. 46 is a top view of one embodiment of an elongated member;

FIG. 47 is a perspective view of the elongated member of FIG. 46 shown with several tines in a bent configuration;

FIG. 48 is a perspective view of an internal support member shown with an elongated member being mounted to the internal support member;

FIG. 49 is a perspective view of an internal support member shown with a second or subsequent elongated member being mounted to the internal support member;

FIG. 50 is a side view of a main body and tine of an elongated member shown with the tine bent out of the plane of the main body;

FIG. 51 is a side view of a main body and tine of an elongated member shown with a tine bend at two locations;

FIG. 62 is a side view of another embodiment of a tissue manipulation tool in accordance with the present disclosure;

FIG. 63 is a cross-sectional view of an intervertebral disc shown with a guide member deployed therein;

FIG. 64 is a cross-sectional view of the intervertebral disc shown with a tissue manipulation tool deployed along the guide member;

FIG. 67 is a cross-sectional view of one embodiment of an endplate preparation device shown inserted with an intervertebral disc space.

DETAILED DESCRIPTION

Figure 5:
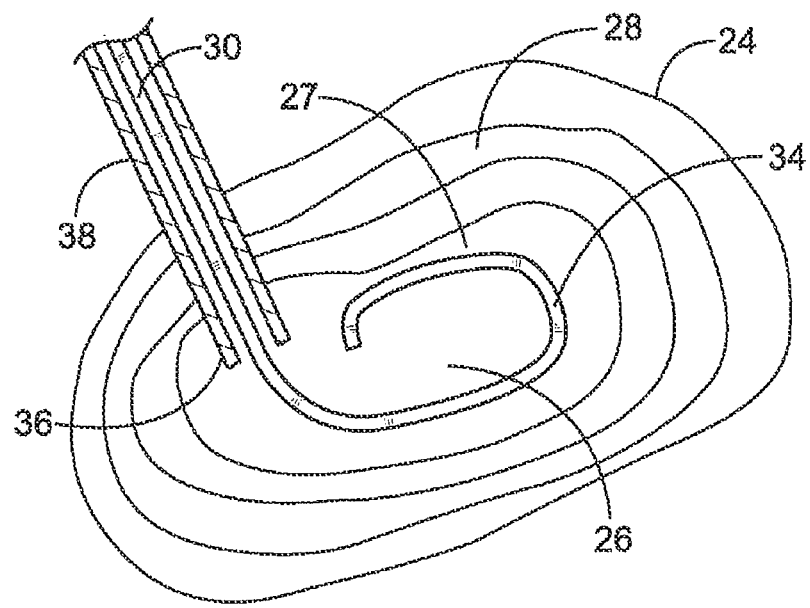
FIG. 5 is a cross-sectional view of the intervertebral disc of FIG. 4, shown with a guide member inserted into the nuclear space.

FIG. 1 illustrates a section of a healthy vertebral (spinal) column, generally designated as 20. Vertebral column 20 includes vertebrae 22 and intervertebral discs 24 separating adjacent vertebrae. Intervertebral discs 24 connect the adjacent vertebra 22 together, providing a joint between the vertebrae that allows movement and flexing of the vertebral column 20. Intervertebral discs 24 also provide a cushion between the adjacent vertebrae 22.

FIG. 2 illustrates a perspective view of one of the intervertebral discs 24 and an associated inferior vertebra 22. The intervertebral disc 24 includes a nucleus pulposus 26 surrounded by an annulus fibrosus 28. The nucleus pulposus 26 is a gelatinous-like material that provides cushioning between adjacent vertebrae. The annulus fibrosus 28 is made up of tougher fiberous material that contains the nucleus pulposus 26 in the nuclear space.

Turning now to the tissue manipulation members or tools, such as the tissue disruption and removal tools of the present disclosure, the tools and methods described herein can be utilized in any number of surgical procedures to cut or otherwise disrupt and remove tissue from a patient, but are particularly well suited for performing endoscopic discectomy procedures and preparing intervertebral discs for prosthetic implantation and spinal fusion. For example, the tissue manipulation tools may be utilized in minimally invasive procedures that are conducted through an access port that has a diameter of between about 0.2 inches (5 mm) and about 0.4 inches (10 mm). The tissue manipulation tools disclosed herein may be made from materials that are visible under x-ray, fluoroscopy or any other suitable imaging system. The tissue manipulation tools may also be made of disposable materials and configured for single use applications. Alternatively, the tissue manipulation tools may be configured as multiple use tools. The manipulation tools may be manually operated or operated by an automated apparatus.

The discectomy and disc preparation tools of the present disclosure generally include a guide member and one or more tissue manipulation devices, such as tissue disruption tools and tissue extraction tools, that can be used in conjunction with each other to cut and remove intervertebral disc tissue. Some examples of tissue disruption tools may include tissue cutting and scraping tools. When in use, the guide member is inserted through the annulus fibrosus and into the nuclear space of an intervertebral disc to provide a generally prescribed pathway for the cutting, scraping and tissue extraction tools to follow. The tools are guided by the guide member, unless the tools are an integral part of the guide member, through the annulus fibrosus and along the generally predefined path into and through the nucleus pulposus region, sometimes referred to as the nuclear space. As each tool is guided by the guide member through the nuclear space, the tool performs its function, i.e., disrupts, cuts, scrapes, grasps or engages tissue, or can be manipulated to perform its function.

FIG. 3 illustrates one embodiment of a guide member 30 that may be comprised of an elongated member, such as a wire, thread or ribbon. The guide member 30 includes a proximal end portion 32 and a distal end portion 34. The distal end portion 34 of the guide member 30 is the portion that is inserted into the nuclear space of the intervertebral disc to provide a structure that can guide the above mentioned cutting, scraping and extraction tools along a desired, pre-defined path through the nuclear space. Preferably, the shape of the distal end portion 34 results in a path that guides the tools to all of the desired locations of the nuclear space required for a particular application. In the embodiment illustrated in FIG. 3, the distal end portion 34 of guide member 30 has a generally elliptical-shaped configuration that can generally follow along the inner wall of the annulus. Alternatively, the guide member can be shaped in an arc or arcuate shape. In one embodiment, the arc shaped guide member is configured to guide the tools from at least the side of the disc where guide member is accessed (ipsilateral) to the opposite side of the disc (contralateral). By repositioning the guide member between anterior and posterior positions, the arc-shaped guide member can guide the tools to all desired locations of the nuclear space. Preferably, the arc shaped guide member is configured so that only moderate repositioning is required to guide the tools to the desired locations for a particular procedure.

Preferably, at least the distal end portion 34 of the guide member 30 is made of a shape memory material, such as a pseudoelastic material, for example Nitinol (NiTi) or other suitable alloy (Cu—Al—Ni, Ti—Nb—Al, Au—Cd, etc.). In other embodiments, the distal end portion can be made from a shape memory polymer. Due to the shape memory characteristics, the guide member 30 can be bent or deformed into a generally linear or straight configuration by inserting or drawing the guide member into a deployment or working cannula. As used herein the term "linear" can refer to perfectly straight or having slight bends or zigzags. When located within the cannula, the guide member 30 takes on and is constrained in the generally linear configuration, so that the guide member can be translated through the cannula for deployment into a patient. When the distal end portion of the guide member exits the cannula, it returns to its generally elliptical-shaped configuration. Thus, because of the guide member's inherent tendency to return to a particular pre-defined shape (i.e., shape memory or pseudoelastic characteristics), the guide member can be deformed prior to or during deployment into a treatment site and then returned to its original shape within the treatment site.

Referring to FIGS. 4 and 5, to deploy the distal end 34 of the guide member 30 into an intervertebral disc 24, the distal end portion 36 of a deployment cannula 38 is inserted through the annulus fibrosus 28 and into or adjacent the nucleus pulposus 26 in nuclear space 27. The insertion of the cannula 38 through the annulus can be through a surgical incision or a pre-existing fissure. Additionally, the deployment cannula 38 can access the intervertebral disc 24 through any suitable access approach. For instance, access for the deployment cannula 38 can be gained through either a posterior lumbar approach, a transforaminal lumbar approach, or a lateral approach. Some procedures may require the deployment of two guide members. In such circumstances, two cannulas can be employed wherein, for example, the first cannula accesses the intervertebral disc from one side, and the second cannula accesses the disc from the other side.

When the discectomy and disc preparation procedures described herein are utilized to prepare the intervertebral disc for endoscopic prosthetic implantation, the size of the surgical access site required for inserting the deployment cannula 38 into the intervertebral disc 24 is preferably not larger than the size of the surgical access site required for implantation of the prosthetic. One of the advantages of utilizing a prosthetic that can be implanted by a minimally invasive endoscopic procedure is that there is less trauma and damage caused to the surrounding tissue. If the access site required for performing a discectomy (or pre-implantation preparation of a disc) is larger than what is required for the endoscopic implantation procedure, then the above-mentioned benefits of the minimally invasive procedure can be diminished. This is especially true when the same access site is used for both the disc preparation procedure and the prosthetic implantation procedure. Accordingly, one of the advantages provided by the tools and procedures described herein are that the access sites needed to perform the procedures are relatively small and similar in size to that required for several of the endoscopic prosthetic implantation procedures. Preferably, the access site has an outer diameter between about 4 mm and about 10 mm. In one embodiment the access site has an outer diameter of about 8 mm. It will be understood that depending on the procedure being preformed that the accesses sites could be larger or smaller than the above range.

Once the deployment cannula 38 is in the desired location, which can be verified through fluoroscopy, the guide member 30 in a generally linear configuration is advanced through the cannula 38. Turning now to FIG. 5, upon exiting the distal end portion 36 of the cannula 38, the distal end portion 34 of guide member 30, by change of configuration, transitions into its generally arcuate shape, such as the partial elliptical-shaped configuration shown. When the guide member 30 is manufactured from materials that are readily visible under fluoroscopy, such as nitinol, the surgeon can use fluoroscopy to ensure that the guide member is delivered along the desired path and is positioned at the desire location. Additionally, the guide member 30 should have sufficient column strength to penetrate the nucleus pulposus 26 and sufficient rigidity to provide a guiding force for the cutting, scraping and extraction tools that will be translated along the guide member 30. The guide member 30 may have different cross-sectional shapes, such as circular, rectangular or other suitable shapes. In one embodiment, the cross-sectional width of the guide member 30, which may be the diameter, is between about 0.04 inch (1 mm) and about 0.1 inch (2.5 mm). The cross-sectional width may also be larger or smaller than this range depending on the particular procedure. Additionally, the size of the guide member may vary along its length to optimize its ability to penetrate only the nuclear tissue while still providing sufficient guiding force for the tools. Furthermore, the distal tip of the guide member may have a feature that facilitates transition through the disc tissue. For example, the guide member could include a blunt or rounded distal end portion that allows it to penetrate soft nucleus material, but prevents it from penetrating the tougher annulus tissue. The dimensions of the ball tipped distal end of the guide member can be varied depending of the column strength of the guide member to reduce the risk of penetration of the guide member into the annulus tissue. Conversely, if desired, the distal tip of the guide member could be configured to penetrate annulus tissue.

Figure 7:
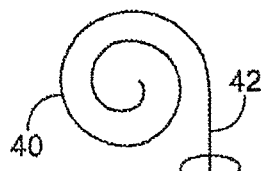
FIG. 7 is a top view of another embodiment of a guide member constructed in accordance with the present disclosure.
Figure 8:
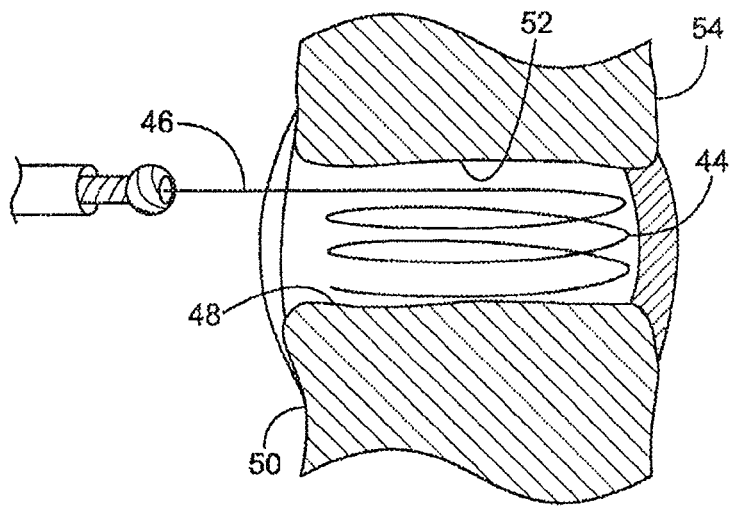
FIG. 8 is a side view of another embodiment of a guide member constructed in accordance with the present disclosure and shown deployed within an intervertebral disc.

Depending on the particular procedure, the location and amount of tissue to be removed, the guide member can have a variety of shapes or configurations, including but not limited to full or partial circular and elliptical shapes, spiral shapes and wavy shapes, and other curved shapes or the guide member, when within the disc space, may have a substantially straight or linear configuration or any other suitable shapes. Additionally, the guide member can have a two dimensional configuration, such as those shown in FIGS. 5, 7, 9 and 10, or a three-dimensional configuration, such as that shown in FIG. 8. FIGS. 7-10 illustrate some of the possible alternative configurations of the guide member. In FIG. 7, the distal end portion 40 of the guide member 42 has a two-dimensional spiral shape that lies in a single plane. In FIG. 8, the distal end portion 44 of guide member 46 has a three-dimensional coiled or helical shape that can have one or more loops and can span from the superior endplate 48 of the adjacent lower vertebral body 50 to the inferior endplate 52 of the adjacent upper vertebral body 54.

Figure 9:
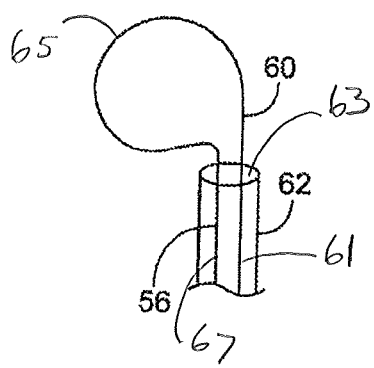
FIG. 9 is a top view of another embodiment of a guide member constructed in accordance with the present disclosure.
Figure 9A:
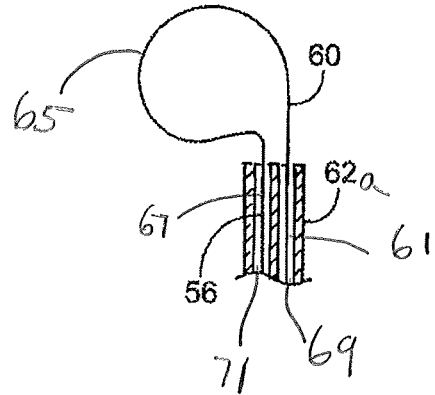
FIG. 9A is a cross-sectional view of one embodiment of a deployment cannula that may be employed to deliver the guide member shown in FIG. 9.
Figure 10:
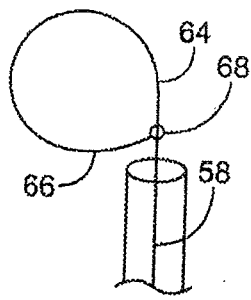
FIG. 10 is a top view of another embodiment of a guide member constructed in accordance with the present disclosure.

FIGS. 9, 9A and 10 show guide members 56 and 58 that have a looped configurations. As shown in FIG. 9, guide member 56 may be moveable through a single lumen cannula 62 and out of the distal end portion of the cannula wherein the distal end portion 60 of guide member 56 defines a continuous loop extending out of and returning into the cannula. In this embodiment, guide member 56 has a first section 61, a second arcuate section 65 and a third section 67 wherein the second arcuate section is between the first and second sections 61 and 67, respectively. First section 61 extends through lumen 63. Second arcuate section 65 extends from and returns back into lumen 63 of cannula 62 to form the continuous looped defined by the distal end portion 60 of guide member 56. The third section 67 of guide member 56 extends back through lumen 63.

In an alternative embodiment, guide member 56 is deployed through a dual lumen cannula 62a, as shown in FIG. 9A. In this embodiment, the cannula 62a includes side-by-side lumens 69 and 71 wherein the first section 61 of guide member 56 extends through lumen 69 and second arcuate section 65 of guide member 56 extends from lumen 69 and returns back into lumen 71 to form the looped configuration of distal end portion 60 of guide member 56. Third section 67 extends through lumen 71 of cannula 62a.

Guide member 58 of FIG. 10 includes a distal end portion 64 having a conjoined loop wherein the terminal end 66 of the guide member includes an eyelet 68 that is connected to the distal end portion 64 of the guide member 58.

Figure 6:
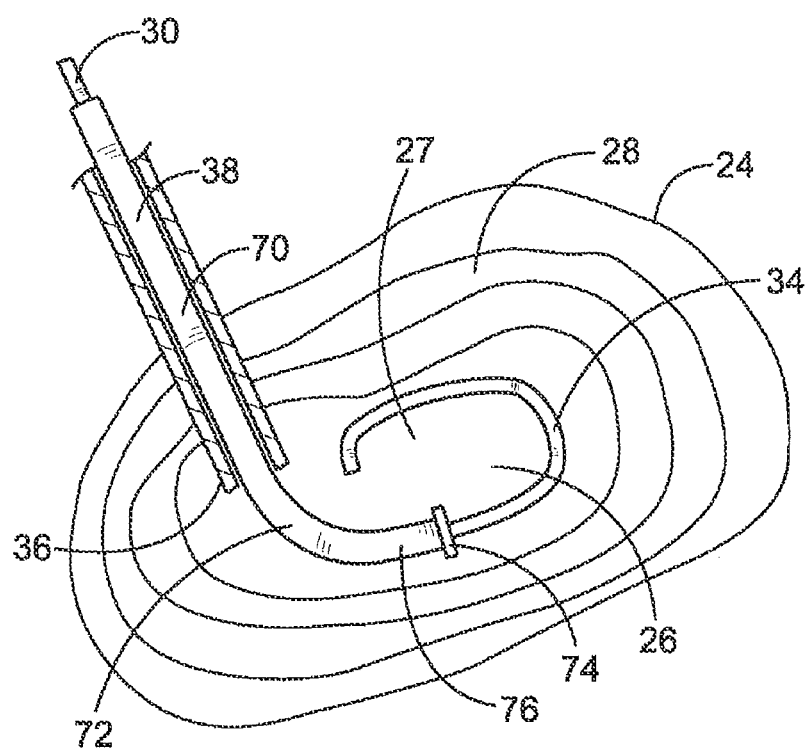
FIG. 6 is a cross-sectional view of the intervertebral disc of FIG. 4, shown with a tissue manipulation tool deployed over the guide member.

Turning now to FIG. 6, after the distal end portion 34 of the guide member 30 is deployed into the nuclear space 27 of intervertebral disc 24, a tissue manipulation tool, such as cutting tool 70, is advanced distally along the guide member 30 and through the deployment cannula 38. When the cutting tool 70 is advanced out of the distal end portion 36 of the deployment cannula 38, it enters the nuclear space 27 and translates along the distal end portion 34 of the guide member 30. The distal end portion 34 of the guide member 30 guides the cutting tool 70 along a predetermined path through the nuclear space 27. Guiding the cutting tool 70 in this manner can provide greater assurance that the cutting tool will reach all of the desired locations for the particular procedure and reduces the risk of accidental injury to the annulus and vertebrae. Preferably, the relationship between the cutting tool 70 and the guide member 30 allows the cutting tool to be translated back and forth along the distal end portion 34 and rotated thereabout. As explained in more detail below, when guide member 56 having a looped configuration as shown in FIGS. 9 and 9a is employed, a tissue manipulation tool may translate along guide member 56 such that the tool translates along the first portion 61 of the guide member through and out of cannula 62/62a. The tool continues to translate along the looped configuration of the distal end portion 60 of the guide member 56 and then re-enters the cannula 62/62a and translates along third section portion 67 of guide member 56 within cannula 62/62a.

Turning back to FIG. 6, as the cutting tool 70 translates along, and optionally rotates about, the guide member 30, it cuts, tears and/or otherwise disrupts the tissue of the nucleus pulposus 26 located in nuclear space 27. Alternatively, if the design of the tissue cutting, disruption, or extraction tool has a preferred mode of operation in just one rotational direction, the proximal handle of the tool may incorporate a one-way ratcheting or clutch mechanism such that it can rotate in only one direction.

In the embodiment of the tissue manipulation or cutting tool 70 shown in FIG. 6, the cutting tool includes an elongated member, such as pushing member 72 which may be, for example, a hollow drive or delivery shaft. The cutting tool 70 also includes a tissue manipulator or manipulation element, such as tissue cutter or cutting element 74, located at the distal end portion 76 of the pushing member 72. The cutting tool 70 is removably associated with the guide member 30 by inserting the guide member 30 into a passageway through pushing member 72 and advancing the cutting tool 70 axially or longitudinally over the guide member 30. The pushing member 72 should have sufficient column strength so as to be distally advanced longitudinally along the guide member 30 and penetrate through nucleus tissue. Preferably, the pushing member 72 also is pullable with minimal stretchability so that is can be easily translated back and forth longitudinally along the guide member 30 and easily withdrawn from the treatment site. Additionally, at least the distal end portion 76 of the pushing member 72 should have sufficient flexibility to translate along the distal end portion 34 of the guide member 30. Optionally, the pushing member 72 can also translate rotation forces from the proximal end (not shown) to the distal end 76, preferably in both clockwise and counterclockwise directions. Preferably, the length of the pushing member 72 is such that manipulation of the proximal end of the pushing member is quickly translated to the distal end portion 76. Also, the pushing members or shafts have a length sufficient to deliver the tissue manipulation elements through a delivery cannula, if one is used, and to the treatment site. In one embodiment, the pushing member is between about 3 cm and about 8 cm in length, and in another embodiment, the pushing member is about 30 cm in length.

The elongated members or pushing members are preferably constructed from a radiopaque material that is visible under fluoroscopy to facilitate observation of its advancement relative to the guide member. The pushing members may also include depth markings on their outer surfaces that allow tracking of advancement into the patient by the naked eye. The internal diameter of the pushing member may be large enough to allow insertion and translation along the guide member. In one embodiment the internal diameter is about 0.07 inch (1.78 mm). The outer diameter of the pushing member may vary and, preferably, is of a size that allows the pushing members to be advanced along the guide member without bucking and/or kinking. In one embodiment, the pushing member has an outer diameter of about 0.2 inch (5.1 mm).

Suitable pushing members or delivery shafts can include, but are not limited to, laser cut hypotubes, multi-layer extrusions shafts that are braided or ribbon reinforced, or counter-wound hollow shafts that include tight inner and outer springs wound in opposite directions. FIGS. 11-13 illustrate some suitable laser cut hypotube shafts, such as a laser cut stainless steel hypotube. The shaft 78 illustrated in FIG. 11 includes a simple spiral cut 80 that provides translation of torque, but only in one direction. The shafts 82 and 84 illustrated in FIGS. 12 and 13 have more complex cut patterns 86 and 88 that can transmit torque in both directions. The cut patterns of these shafts can vary in width and pitch to optimize mechanical performance and the ability to track over guide members of varying size and shape. FIGS. 14 and 15 illustrate exemplary embodiment of multi-layer extruded shafts 90 and 92 with braided or ribbon reinforcement. The multi-layer extruded shafts are reinforced with metal wire or ribbon to provide a flexible, but torqueable shaft.

Optionally, the proximal end portion of the hollow pushing member or shaft can be operatively connected to a suction source to provide a suction force at the distal end portion of the shaft. The suction force can be used to draw tissue to be disrupted toward the cutting element. Additionally, the suction force can be used to draw disrupted tissue into the distal end portion of the shaft and through the shaft to remove the disrupted tissue from the intervertebral disc.

Turning now to the tissue manipulators or manipulating elements of the tissue manipulation tool. The tissue manipulation elements may be associated with the distal end portion of the elongated pushing member and in one embodiment can be attached thereto. Preferably, the tissue manipulators or manipulating elements have a shape that is conducive to translating along the curved path of the distal end portion of the guide member and/or have sufficient flexibility that allows translation along the curved path. The manipulation elements also have sufficient rigidity to effectively disrupt tissue, such as by cutting or scraping, and/or capture and remove tissue.

The tissue manipulation elements disclosed herein may include two or more sections wherein each section is particularly suited for manipulating a particular type of tissue. In one embodiment, the manipulation element has two or more sections that are arranged relative to each other along the length of the manipulation element wherein each section is particularly suited for manipulating a particular type of tissue such that the tissue manipulation element has differing manipulation features along the length of the element. In other embodiments, the different sections may be arranged circumferentially relative to each other around the tissue manipulation element such that the manipulation element has different manipulation features circumferentially along the tissue manipulation element.

The tissue manipulation element may include tissue disruptors or disruption elements, including but not limited to blades, edges, tines, wires, tangs or bristles, that are suitable for disrupting (including abrading) intervertebral disc tissue and/or the vertebral endplates adjacent to the disc space. The tissue manipulation elements also may include tissue capturing elements for capturing and removing tissue from the disc space.

The tissue manipulation element may include any combination of tissue disruption elements and/or capturing elements. For example, the tissue manipulation element may include two or more different types of disruption elements or include two or more different types of tissue capturing elements. In other embodiments, the tissue manipulation element includes a disruption element and a capturing element. In one embodiment, the tissue manipulation element includes a disruption element(s) that is suitable for disrupting intervertebral disc tissue and a disruption element(s) that is suitable for disrupting (including abrading) vertebral endplates. The different types of disruption elements may be in any suitable arrangement. For example, the disruption elements may be arranged such that the vertebral disc tissue disruption elements are located at or near one end of the tissue manipulation element and the endplate disruption elements are located at or near the other end of the disruption elements. In one embodiment, the disc tissue disruption elements are located at or near the distal end of the manipulation element and the endplate disruption elements are located at or near the proximal end. In yet another embodiment, the different types of disruption elements may be arranged circumferentially around the tissue manipulation element or in an alternating pattern or a helical or screw-like pattern on the tissue manipulation element. In a further embodiment, the differing types of tissue disruption elements may be randomly arranged on the tissue manipulation element.

When the tissue manipulation elements are tissue disruptors or disruption elements, such as cutting and/or scraping elements, the tissue disruptors may include one or more blades or bladed edges having tissue manipulation surfaces that are suitable for contacting and cutting and/or scraping intervertebral disc tissue. The tissue manipulation surfaces are preferably particularly well suited for cutting nucleus pulposus tissue and scraping vertebral endplates adjacent to the disc space. The tissue manipulation surfaces may be spaced or at least partially spaced in a radial direction from the outer surface of the pushing member and/or from the central axis of the tissue manipulation element and/or from the rotational axis of the manipulation element when the manipulation element is configured to rotate. The profile of the blades may be flat or curved and the shape of the blades C-shaped, L-shaped or otherwise shaped. Additionally, the blades or cutting edges can be serrated or smooth. The blades also can be substantially rigid at or near the point of attachment of the cutting element to the pushing member and more flexible toward the distal ends of the blades so that the blades do not inadvertently damage the annulus or the endplates of adjacent vertebra.

Figure 26:
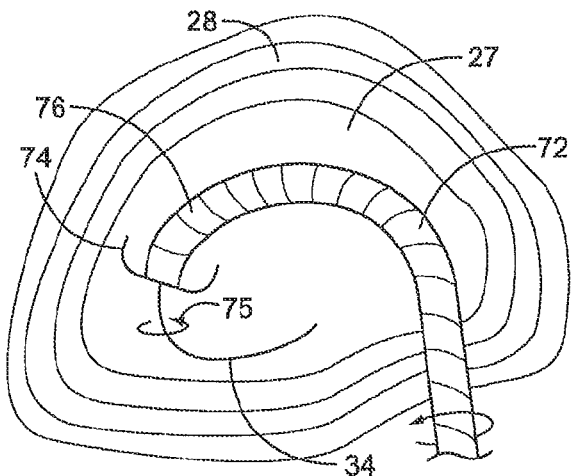
FIG. 26 is a schematic illustration of one embodiment of a tissue manipulation tool rotating about a guide member within the nuclear space of a disc.

FIGS. 16-21 show examples of tissue manipulation or cutting elements 96, 98, 100 that can be associated with the distal end portion of the pushing member of a tissue manipulation tool, such as be attachment thereto. The illustrated embodiments of the tissue cutters or cutting elements of these figures include a hole or passageway 94 for passage of the guide member therethrough. The passage of the guide member through the hole allows the cutting elements to rotate about the guide member. Referring to FIGS. 17, 19 and 21, the axis of rotation of each cutting element, which in some embodiment may also be the central axis of the cutting element, is designated as 102. Referring to FIG. 26, as the cutting tool 70 is advanced longitudinally over the distal end portion 34 of guide member 30, the proximal end portion 74 of pushing member 70 can be rotated by hand or machine. The rotational forces are translated along the pushing member 70 to the distal end portion 76 of the pushing member 72, resulting in rotation of cutting element 74 as indicated by arrow 75.

Referring back to FIG. 16, the tissue cutter or cutting element 96 has a generally elongated front face in which the passageway 94 for receiving the guide member is located therethrough. As shown in FIG. 17, the cutting element 96 may be a U-shaped strip of material having a thin, flat profile. Alternatively, the cutting element 96 may have a thicker profile or a block-like configuration. Edges 104 and 106 have tissue manipulation surfaces 95 that contact and cut or otherwise disrupt tissue. The tissue manipulation surfaces are spaced or at least partially spaced in a radial direction from the outer surface of the pushing member 70. The tissue manipulation surfaces may also be spaced in a radial direction from the axis of rotation 102 and/or from the central axis of the cutting element. The edges 104 and 106 may be bladed edges or sharp edges that are designed to cut or otherwise disrupt nucleus pulposus tissue as the cutting member 96 is advanced along and/or rotated about the guide member.

The cutting element 98 of FIGS. 18 and 19 has a generally cruciform shape with the passageway 94 located through the center of the cruciform. Cutting element 98 may have a thin profile or may have a block-like configuration Each appendage 108, 110, 112, 114 of the cruciform includes one or more bladed edges 115 having tissue manipulation surfaces 97 that contact and cut or otherwise disrupt nucleus tissue as the cutting element 98 is advanced along and rotated about the guide member. As shown in FIG. 19, the tissue manipulation surfaces are spaced or at least partially spaced in a radial direction from the outer surface of the pushing member. The tissue manipulation surface may also be radially spaced from the axis of rotation 102 and/or from the central axis of cutting element 98.

Cutting element 100 of FIGS. 20 and 21 may be an L-shaped strip of material having a thin profile. Alternatively, cutting element 100 may have a thick profile or a block-like configuration. The passageway 94 for receiving the guide member is located through the front face 116 of the cutting element 100. Similar to the other cutting elements, cutting element 100 includes edges 118 and 120 having tissue manipulation surfaces 99 that contact and cut or otherwise disrupt nucleus tissue as the cutting element is advanced along and rotated about the guide member. Edges 118 and 120 may be bladed or sharpened to assist in cutting the tissue. Additionally, as shown in FIG. 21, the tissue manipulation surfaces are spaced or at least partially spaced in a radial direction from the outer surface of the pushing member and/or from the axis of rotation.

FIGS. 22-25 illustrate other embodiments of tissue manipulation tools, such as the illustrated cutting tools. In the embodiments shown the cutting element includes as least one outwardly extending curved blade that is attached to the distal end portion of the pushing member at two locations. The blade includes at least one tissue manipulation surface 89 that contacts and cuts or otherwise disrupts tissue. The tissue manipulation surface is spaced or at least partially space in a radial direction from the outer surface of the pushing member 128. The tissue manipulation surface also may be radially spaced from the axis of rotation 129 and/or the central axis of cutting tool 122. Referring to FIG. 22, the cutting tool 122 includes a cutting element 124 attached to the distal end portion 126 of pushing member 128, which can be any of the shafts described herein or any other suitable pushing member. The cutting element 124 includes a blade 130 that has a proximal end portion 132 and a distal end portion 134. The distal end portion 134 of blade 130 can be attached at or near the distal tip 136 of the shaft 128 and the proximal end portion 132 of the blade 130 can be attached to the distal end portion 126 of the pushing member 128 at 138. In the illustrated embodiment, the distal end portion 134 of the blade 130 is affixed to a first collar 140 attached to the distal tip 136 of the pushing member 128. The proximal end portion 132 of the blade 130 is slidably attached to a second collar 142 located proximal the first collar 140. The proximal end portion 132 of the blade 130 is slidably located between the second collar 142 and the pushing member 128. The proximal tip 144 of the blade 130 includes a bent or curled tail section that engages the second collar 142 to prevent the proximal end portion 132 of blade 130 from sliding distally past the second collar 142. Thus, the proximal end portion 132 of blade 130 is slidably trapped between the pushing member 128 and the second collar 142. FIG. 23 illustrates an alternative embodiment of the cutting tool in which the tool 146 includes a first blade 130 and a second blade 148, in a two or opposing dual blade configuration.

FIG. 25 shows one embodiment of the slip fit attachment between the proximal ends of blades 130 and 148 and the second collar 142 for the dual blade cutting tool shown in FIG. 23. The second collar 142 can be attached to opposed sides of the pushing member 128 at attachment locations 150 and 152, leaving spaces or slots 154 and 156 between the collar 142 and the pushing member 128. The collar 142 can be attached to the pushing member 128 in any suitable fashion, such by welding, solder or with the use of suitable adhesives. The proximal end of blade 130 is located in slot 154 and proximal end of blade 148 is located in slot 156. The proximal tips of the blades 130 and 148 can be pre-curled or curled after insertion into slots 154 and 156.

Referring to FIG. 24, the slip fit connection between the blades 130 and 148 and the pushing member 128 enhances the cutting tool's ability to translate over the curved portions of the distal end portion 34 of guide member 30. As the distal end portion 126 of pushing member 128 translates over the distal end portion 34 of the guide member 30, the proximal end portion 160 of blade 148, located on the inside of the curve, moves proximally away from collar 142 and the proximal end portion 132 of blade 130, located on the outside of the curve, moves distally until it engages collar 142. Additionally, referring back to FIG. 23, the cutting tool can also be rotated about guide member 30.

FIG. 31 illustrates another embodiment of a tissue manipulation element 101 that may be used for cutting tissue and/or capturing tissue for removal. Tissue manipulation element 101 includes a tubular member 103 and a plurality of blade members 105 having tissue manipulation surfaces. The blade members 105 may be elongated members, such as ribbons or wires. The ends 107 of the blade members 105 are connected to the tubular member 103. The blade members 105 may be flat elongated members or rounded elongated members. Additionally, the blade members 105 may have a variety of surface configurations, such as sharp bladed surfaces, serrated surfaces or blunt surfaces. The blade members 105 form a whisk-like configuration. In the embodiment shown, each of the blade members 105 extends from the tubular member 103 and doubles back to form the whisk-like arrangement. Tissue manipulation element 101 may be located on the distal end of an elongated member or pushing member 70, which may be any of the delivery shafts described herein or any other suitable pushing member. Furthermore, the tissue manipulation surfaces of the blade members 105 are spaced or at least partially spaced in a radial direction from the outer surface of the pushing member. It will be understood that the pushing member does not necessarily need to be directly adjacent to the tissue manipulation surface for such surface to be spaced in a radial direction from the outer surface of the pushing member, and that the tissue manipulation surface can be spaced both laterally and radially from the outer surface of the pushing member. The tissue manipulation surfaces also may be space in a radial direction from the axis of rotation 179 and/or the central axis of the tissue manipulation element 101. The pushing member may be used to guide the tissue manipulation element 101 along the guide member and into and through disc tissue.

When a guide member is utilized to deploy tissue manipulation element 101, the guide member is inserted through a passage of the pushing member and through tubular element 103 and one of the spaces or openings 109 between adjacent blade members 105. In this arrangement, the pushing member may be used to push the tissue manipulation element 101 along the guide member. When the tissue manipulation element 101 is being used as a cutting element, the blade members 105 preferably are sufficiently flexible to accommodate being advanced along the contour of the guide member and yet rigid enough to cut or otherwise disrupt tissue, such as nuclear and/or endplate tissue. Similar to the above described embodiments, rotation of the pushing member results in rotation of the tissue manipulation element 101 about the guide member. As the tissue manipulation element 101 is rotated about a curved portion of a guide member, the blade members 105 on the inside of the curve of the guide member bow outward and engage tissue, while those on the outside of the curve deform into a more straight configuration that slightly engages tissue. As tissue manipulation element 101 is rotated, blade members 105 engage and cut or otherwise disrupt the tissue. Additionally, blade members 105 of tissue manipulation element 101 can be configured so that as the manipulation element 101 rotates, disrupted tissue becomes captured in the inner space 111 generally defined by the blade members 105 for removal of the disrupted tissue. Thus, the tissue manipulation element 101 may be used as a cutting and extracting tool.

When tissue manipulation element 101 is employed as a tissue removal or extraction tool, the tissue manipulation element 101 may be used to capture and remove tissue that has been cut by tissue manipulation element 101. Alternatively, the tissue manipulation tool may be is inserted into the nuclear space to capture and remove tissue that has been previously disrupted by another cutting tool. When used as both a cutting and removing tool, the blade members 105 of tissue manipulation element 101 may be similar to that described above. When used primarily as a tissue removal tool, the blade members 105 of tissue manipulation element 101 can be generally rounded and substantially blunt, so as to reduce the element's ability to cut tissue. As the tissue manipulation element 101 is rotated, previously disrupted tissue becomes captured within the space 111 generally defined by the blade members 105. The rounded blade members 105 of the tissue manipulation element 111 may still disrupt some tissue and the amount of tissue that the blade members 105 disrupt can be controlled by their configuration. When the desired amount of tissue is captured, the tissue manipulation element 101 is removed. The tissue manipulation element 101 can be cleaned and reinserted, or a new unused tissue manipulation element can be inserted to collect more tissue.

In an alternative embodiment, that does not necessarily require the use of a guide member, tissue manipulation element 101 may be located at the distal end portion of a pushing member, such as an elongated rod or shaft, that may be inserted through a cannula and into a treatment site without the use of a guide member. Preferably, the elongated rod can transmit torque applied to the proximal end portion of the elongated rod to the distal end portion of the rod to rotate the tissue manipulation element. In one embodiment, at least the distal end portion of the elongated rod is constructed of a shape memory material, such as nitinol. When constructed from a shape memory material, the distal end portion of the elongated rod may be pre-set into an arcuate or other non-linear configuration that can be straightened into a generally linear configuration to be passed through a cannula for deployment into the treatment site. As the distal end portion of the elongated rod exits the cannula, it returns to its generally non-linear configuration, directing the tissue manipulation element 101 to the desired location.

Referring to FIG. 32a, there is shown another embodiment of a tissue manipulation element 113 that may be used as a cutting element and/or a tissue extraction element. Similar to the tissue manipulation elements described above, tissue manipulation element 113 may be located at the distal end of a pushing member 70, such as any of the delivery shafts disclosed herein or any other suitable pushing member. For example, the tissue manipulation element 113 may be located at the distal end portion of a hollow tubular shaft for deployment over a guide member, or tissue manipulation element 113 may be located at the distal end of an elongated rod that may or may not have a predefined shape and does not require the use of a guide member for deployment or placement within a treatment site.

Tissue manipulation element 113 includes a proximal end portion 115, a distal end portion 117 and a plurality of blade members 119 extending therebetween. Preferably, tissue manipulation element 113 includes at least a pair of blade members 119. The blade members 119 may be elongated strips of material that extend generally longitudinally between the proximal end portion 115 and the distal end portion 117. Generally longitudinally extending slots 121 are located between adjacent blade members 119. Preferably, the tissue manipulation element 113 has at least one pair of slots. It should be understood, however, that tissue manipulation element 113 may have any number of slots and that the number of slots depends on the number of blade members. The blade members 119 include a middle section 123 that is bowed outwardly and a tissue manipulation surface that is spaced or at least partially spaced in a radial direction from the outer surface of the pushing member 70. The tissue manipulation surfaces also may be radially spaced from the axis of rotation 189 of the tissue manipulation element and/or the central axis of the tissue manipulation element. The blade members 119 can be of virtually any configuration, such as a flat configuration, a rounded configuration or a combination thereof. Additionally, the surfaces of the blade members are preferably configured for cutting, tearing or otherwise disrupting tissue. As such, the surfaces of the blade members 119 can include sharp or bladed edges, serrations, teeth or the like.

When the tissue manipulation element 113 is configured to be guided into and through tissue of a treatment site by a guide member, the proximal end portion 115 and the distal end portion 117 may be generally tubular shaped members that each end portion 115 and 117 include a passageway for receiving the guide member. The guide member is inserted through the passageway of the proximal end portion 115 through the inner space 125 defined by the blade members 119 and through the passageway of the distal end portion 117 so that the tissue manipulation element 113 can be advanced over the guide member and rotated about the guide member. Preferably, the blade members 119 are constructed of a material that has sufficient flexibility to allow the cutting element 113 to follow along the contour of the guide member. When used a cutting tool, the tissue manipulation element 113 may be rotated about the guide member to cut or otherwise disrupts tissue. In one embodiment, the slots 121 and the blade members 119 can be configured so that the cut tissue is collected within the interior cavity or space 125 generally defined by the blade members 119 for removal from the treatment site.

In one embodiment, tissue manipulation element 113 may be transformable from a first or deployment configuration to a second or deployed configuration shown in FIG. 32a. It will be understood, however, that the tissue manipulation element 113 is not necessarily transformable and could just have the single configuration illustrated in FIG. 32a. Referring to FIG. 32b, in the deployment configuration, the tissue manipulation element 113 can have a generally tubular or cylindrical shape with the blade members 119 extending in a generally linear or straight configuration. The deployment configuration allows the tissue manipulation element 113 to easily travel through a deployment cannula or through an endoscopic access site. To transform the tissue manipulation element 113 from the deployment configuration to the deployed configuration, the proximal end and distal end portions 115 and 117 are compressed or moved toward each other. As the proximal end and distal end portions 115 and 117 move toward each other, the blade members 119 bow outwardly. In one embodiment, the tissue manipulation element 113 may be made from a shape memory material that has a natural tendency to form the deployed configuration.

In the embodiment shown in FIG. 32b, the tissue manipulation element 113 includes a pull/stop member 127, such as the illustrated wire. The pull/stop member 127 may also be an elongated tube or other elongated element. The pull/stop member 127 assists in facilitating the movement of the proximal and distal end portions 115 and 117. In the embodiment shown, the pull/stop member 127 extends through the tissue manipulation element 113 and is attached to the distal end portion 117 of the tissue manipulation element. To facilitate relative movement of the distal end portion 117 toward the proximal end portion 115, the proximal end portion 115 is held in a stationary position, by for example a pushing member, and the pull/stop wire 127 is pulled to move the distal end portion 117 toward the proximal end portion 115. Alternatively, the proximal end portion 115 can be moved toward the distal end portion 117 by utilizing the pull/stop wire 127 to hold the distal end portion 117 in a stationary position while advancing the proximal end portion 115 toward the distal end portion 117, by for example, advancement of a pushing member associated with the proximal end portion 115.

When in operation, the tissue manipulation element 113 may be located at the distal end portion a pushing member, such as any of the delivery shafts described herein or any other suitable pushing member. Similar to the embodiments discussed above, the guide member can be deployed into a treatment site. The guide member then may be inserted into and through a passageway of the pushing member and through tissue manipulation element 113. With the tissue manipulation element 113 in the deployment configuration, the pushing member may then be used to advance the tissue manipulation element 113 along or over the guide member and into the treatment site. Once in the treatment site, the pull/stop member 127 is utilized to facilitate transforming the tissue manipulation element 113 from the deployment configuration to the deployed configuration. In the deployed configuration, the tissue manipulation element 113 can be rotated about and translated back and forth along the guide member to cut or otherwise disrupt tissue. After a desired amount of tissue has been disrupted, the disrupted tissue can then be collected within the slots 121 between the blade members 119 and in inner cavity 125 defined by the blade members 119. The pull/stop member 127 can be utilized to return the tissue manipulation element 113 to the deployment configuration. As the tissue manipulation element 113 returns to the deployment configuration, the blade members 119 return to their generally linear configuration and the middle sections 123 of each blade member 119 move inwardly, closing down the slots 121 and reducing the size of the inner cavity 125 generally defined by the blade members 119. As the middle sections 123 of the blade members 119 move inwardly, the disrupted tissue becomes trapped within the slots 121 and the inner cavity 125. The tissue manipulation element 113 and pushing member can then be retracted and removed from the treatment site, thereby removing the tissue captured by and within the tissue manipulation element 113. It will be understood that tissue manipulation element 113 may be also used primarily as a tissue removal tool to removal tissue that has been cut or otherwise disrupted by another cutting tool.

FIG. 33 illustrates another embodiment of a tissue manipulator or manipulation element 131 that can be used as a cutting tool and/or a tissue extraction tool. In this embodiment, the tissue manipulation element 131 includes a proximal end portion 133, a distal end portion 135 and a plurality of blade members 137, extending therebetween. Blade members 137 may be elongated members, such as wires, ribbons or rods, and have tissue manipulation surfaces. The blade members 137 can have a round configuration or a flat configuration. Additionally, the blade members 137 can include sharp surfaces, serrated surfaces or dull or blunted surfaces. The tissue manipulation surfaces of the blade members 137 are spaced or at least partially space in a radial direction from the outer surface of pushing member. The tissue manipulation surfaces also may be radially spaced from the central axis of the tissue manipulation element 131 and/or the central axis of the manipulation element.

Similar to the previously discussed tissue manipulation elements, tissue manipulation element 131 can be located on the distal end of an elongated member or pushing member 70, such as any of the delivery shafts disclosed herein or any other suitable pushing member. For example, the tissue manipulation element 131 can be located on the distal end of a delivery shaft and configured to be translated over a guide member or the tissue manipulation element 131 can be located at the distal end portion of an elongated delivery rod, which does not necessarily require the use of a guide member. When the tissue manipulation element 131 is configured to be advanced along or over a guide member, the proximal end and distal end portions 133 and 135 of the tissue manipulation element 131 may have a generally tubular-like shape with a passageway therethrough. The guide member is inserted through the passageway of the proximal end portion 133, through the inner space 139 generally defined by the blade members 137 and through the passageway of the distal end portion 135 so that the tissue manipulation element 131 may be easily translated or tracked along the guide member.

In one embodiment, tissue manipulation element 131 may be transformable between a first or deployment configuration and a second or deployed configuration. It will be understood, however, that the tissue manipulation element 131 is not necessarily transformable and could just have the single configuration illustrated in FIG. 33. In the deployment configuration, the blade members 137 are extended and generally linear or straight. The deployment configuration allows the tissue manipulation element 131 to easily travel through a deployment cannula or through an endoscopic access site. To transform the tissue manipulation element 131 from the deployment configuration to the deployed configuration, the proximal end and distal end portions 133 and 135 are compressed or moved toward each other. As the proximal end and distal end portions 133 and 135 are move toward each other, the blade members 137 bow or buckle outwardly so that the blade members 137 can effectively contact and cut tissue.

In one embodiment, the tissue manipulation element 131 can be made from a shape memory material that has a natural tendency to form the deployed configuration. Alternatively, the tissue manipulation element 131 could include a pull/stop mechanism similar to the one described above with respect to FIG. 32b.

In operation, the tissue manipulation element 131 can be located at the distal end portion of a pushing member, such as any of the delivery shafts described herein or any other suitable pushing member. Similar to the embodiments discussed above, a guide member is inserted through a cannula and into a treatment site. The guide member is then inserted into and through the pushing member and tissue manipulation element 131, and the pushing member is used to advance the tissue manipulation element along or over the guide member and into the treatment site. Once in the treatment site, the tissue manipulation element 131 is transformed from the deployment configuration to the deployed configuration. In the deployed configuration, the tissue manipulation element 131 can be rotated about and translated longitudinally back and forth along the guide member to cut or otherwise disrupt tissue with the blade members 137. After a desired amount of tissue has been disrupted, the tissue manipulation element 131 can be transformed back into its deployment configuration to capture, trap or ensnare disrupted tissue between the blade members 137 and within the inner space 139 generally defined by the blade members 137. As the tissue manipulation element 131 returns to the deployment configuration, the blade members return to their generally linear, extended configuration, thereby trapping tissue within the inner cavity 139. The tissue manipulation element 131 and delivery shaft can then be retracted and removed from the treatment site, thereby removing the tissue captured by and within the tissue manipulation element 131. It will be understood that tissue manipulation element 131 can be also used primarily as a tissue removal tool to removal tissue that has been cut or otherwise disrupted by another cutting tool.

Figure 35:
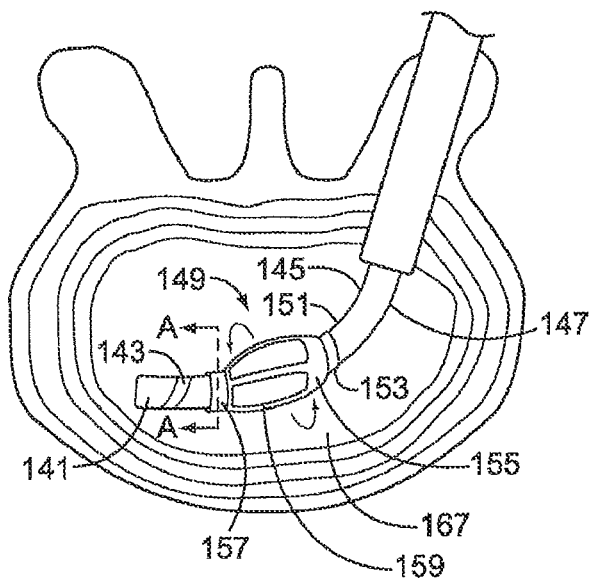
FIG. 35 is a top view of a tissue manipulation tool deployed along the guide member of FIG. 34.
Figure 36:
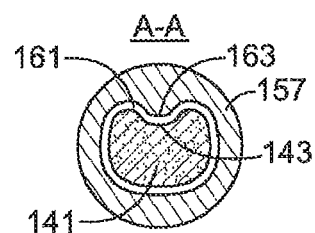
FIG. 36 is a cross-sectional view of the tissue manipulation tool and guide member taken along line A-A of FIG. 35.

FIGS. 34-36 illustrate an alternative embodiment of a guide member 141 and an associated tissue manipulation tool 145. Referring to FIG. 34, the guide member 141 is generally similar to the guide members previously discussed herein, except that the surface of the guide member 141 defines a groove or indent 143 that extends along and around the guide member 141 in a generally helical configuration. Similar to the previous embodiments, the guide member 141 can be have any number of various configurations and can be made from a shape memory material that can be pre-set into a desired shape.

Referring to FIG. 35, the tissue manipulation tool 145 includes a pushing member 147, such as the elongated hollow tubular delivery shaft, having a rotatable tissue manipulator or manipulation element 149 located at the distal end portion 151 of the pushing member 147. The pushing member 147 may be any of the delivery shafts described herein or any other suitable pushing member. Similar to the previous embodiments, the pushing member 147 includes a lumen for insertion of the guide member 141 so that the pushing member 147 can be translated along or over the guide member. Preferably, the pushing member 147 has sufficient flexibility to be advanced along the contour of the guide member 141 and sufficient column strength to advance the tissue manipulation element 149 along the guide member 141.

The tissue manipulation element 149 may be any suitable manipulation element, such as a tissue disruption element, for example, a cutting element or scraping element. The tissue manipulation element 149 may also be a tissue removal element. The tissue manipulation element 149 is rotatably coupled to the distal end portion 151 of the pushing member 147 so that the tissue manipulation element 149 rotates independently of and relative to the pushing member 147. In the embodiment shown, the tissue manipulation element 149 is attached to the pushing member 147 by a rotatable coupling 153, which may be any suitable rotatable coupling.

In the illustrated embodiment of the tissue manipulation tool 145, the tissue manipulation element 149 is a tissue cutting element, which includes a proximal end portion 155, a distal end portion 157 and a plurality of blade members 159 extending therebetween. The blade members 159 include tissue manipulation surfaces that are spaced or at least partially spaced in a radial direction from the outer surface of the pushing member and/or from the rotational axis of the tissue manipulation element and/or from the central axis of the tissue manipulation element. The proximal end portion 155 of the tissue manipulation element 149 is rotatably connected to the distal end portion 151 of the pushing member 147 by the rotatable coupling 153. The proximal end and distal end portions 155 and 157 of the tissue manipulation element 149 shown each includes a passageway for insertion of the guide member 141 so that the tissue manipulation element 149 may be translated along the guide member 141. Referring to FIG. 36, the inner wall 161 of the distal end portion 157 that defines the passageway includes a protrusion or projection 163 that engages and rides or follows along the groove 143 of the guide member 141. In will be understood that protrusion 163 that engages the groove 143 does not necessarily have to be associated with the distal end portion 157 of the tissue manipulation element 149, for example, the inner wall of the proximal end portion 155 defining the passageway could include a projection that engages the groove. Alternatively, both the proximal end and distal end portions 155 and 157 may include a projection that engages the groove, or one or more groove engaging projections may be located at any other suitable location along the tissue manipulation tool. As the tissue manipulation element 149 is translated along or over the guide member 141, the protrusion 163 of the inner wall 161 of the distal end portion 157 of the tissue manipulation element 149 rides in or along the helical groove 143 on the guide member 141, which results in rotation or spinning of the tissue manipulation element 149 about the guide member 141. The rate of rotation of the tissue manipulation element 149 can be varied by varying the distance between the coils 165 of the groove 143 extending along and around the guide member 141.

FIGS. 34 and 35 illustrate one exemplary use of the tissue manipulation tool 145 within an intervertebral nuclear space 167. Referring to FIG. 34, the distal end 169 of a delivery cannula 171 is inserted into the nuclear space 167 and the guide member 141 is then deployed through the cannula 171 and into the nuclear space 167. The pushing member 147 is then employed to advance the tissue manipulation element 149 over the guide member 141, through the cannula 171 and into the nuclear space 167. As the tissue manipulation element 149 is advanced over the guide member 141, the protrusion 163 of the distal end portion 157 of the tissue manipulation element 149 follows along groove 143, and the tissue manipulation element 143 rotates about the guide member 141. When the tissue manipulation element 149 is retracted along the guide member 141, the tissue manipulation element 149 rotates in the other direction. As mentioned above, in the embodiment shown, the tissue manipulation element 149 is a cutting element and as the tissue manipulated element 149 is rotated about the guide member 141, blades 159 contact and cut or otherwise disrupt tissue. After the desired amount of tissue have been cut or otherwise disrupted, the tissue manipulation tool 149 is removed.

Figure 27:
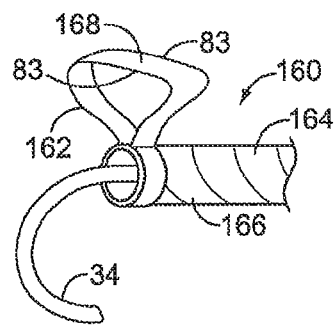
FIG. 27 is a perspective view of an other tissue manipulation tool constructed in accordance with the present disclosure.
Figure 28:
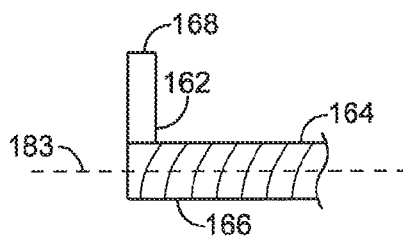
FIG. 28 is a side view of the tissue manipulation tool of FIG. 27.
Figure 29:
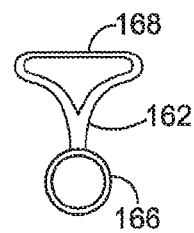
FIG. 29 is a front end view of the tissue manipulation tool of FIG. 27.

FIGS. 27-29 illustrate an embodiment of a tissue manipulation tool 160 that can be employed as a scraping tool that is particularly well suited for scraping, cutting or otherwise disrupting endplate tissue, but can also be employed to disrupt nucleus tissue. In several vertebral fusion procedures, a fusion prosthetic implant is implanted into the disc. Bone material, such as bone graft, is then placed adjacent to the implant. The prosthetic maintains the height of the intervertebral disc as the bone graft material promotes bone growth that fuses the endplates of adjacent vertebrae together. It has been discovered that cutting, scraping or otherwise disrupting the surface of the adjacent endplates and causing them to slightly bleed, promotes bone growth and fusion, which can reduce the patient recovery period.

Tissue manipulation tool 160 includes a tissue manipulator or manipulation element 162 and a pushing member 164, which can be any of the elongated shafts described herein.

The pushing member 164 includes a proximal end portion (not shown) and a distal end portion 166. Tissue manipulation element 162 is a tissue scraper that has a generally looped blade 168, which is generally similar to a ring-curette. Preferably, the blade 168 is constructed from a flexible, super-elastic material such as nitinol or other similar alloys. The looped blade 168 includes at least one tissue manipulation surface 83 that contacts and disrupts tissue. The tissue manipulation surface is spaced or at least partially spaced in a radial direction from the outer surface of pushing member 164. The tissue manipulation surface also may be radially spaced from the axis of rotation 183 of the tissue manipulation element and/or the central axis of the scrapping tool.

The tissue manipulation tool 160 is capable of being advanced over the guide member through cannula 38 and into the nucleus space. As illustrated in FIG. 27, the tissue manipulation tool 160 can be translated over the distal end portion 34 of the guide member. Once in the nucleus space, the blade 168 of the tissue manipulation element 162 can be orientated so that the top portion of the blade contacts the surface of either one of the endplates of the adjacent vertebrae. When the blade 176 is made from flexible materials, the blade can flex to accommodate a range of disc heights. Once in the desired orientation, the tissue manipulation tool 160 can be cycled back and forth to disrupt the surface of the endplate, causing the surface to bleed. After the surface of one of the endplates has been disrupted, the tissue manipulation tool 160 can be rotated so that the top portion of the blade 168 contacts the surface of the other endplate. The tissue manipulation element 162 can be rotated by applying torque to the proximal end of the pushing member 164. The tissue manipulation tool 160 is again cycled back and forth to disrupt the surface of the endplate. After the surfaces of the adjacent endplates have been disrupted, the tissue manipulation tool 160 is retracted along the guide member and removed from the intervertebral disc.

Figure 30:
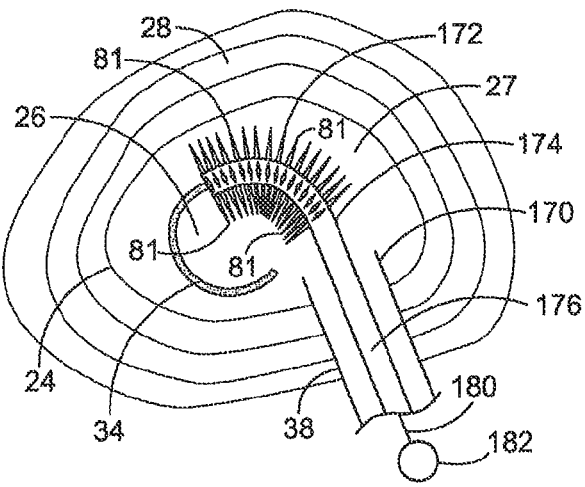
FIG. 30 is top view of yet another embodiment of a tissue manipulation tool constructed in accordance with the present disclosure and shown deployed within a disc space.

FIG. 30 illustrates another embodiment of a tissue manipulation tool 170. The manipulation tool 170 includes a tissue manipulation element or section 172 carried on the distal end portion 174 of an elongated member 176, which may be any of the shafts described herein or any other suitable pushing member of sufficient strength to insert and rotate the tissue manipulation element, if desired. The tissue manipulator or manipulation element 172 includes a plurality of tissue engaging brush-like elements, such as tines or bristles 178 for disrupting, disaggregating or capturing tissue. The tissue manipulation element includes tissue manipulation surfaces 81 that contact the tissue for disrupting or capturing tissue. The tissue manipulation surfaces are spaced or at least partially spaced in a radial direction from the outer surface of the pushing member 176. The tissue manipulation surface may also be spaced in a radial direction from the axis of rotation of the tissue manipulation element and/or the central axis of the tissue manipulation element.

Depending on the desired procedure, the tissue manipulation element 172 may be used to disrupt tissue, such as by cutting or scraping, and/or may be used to capture or grab tissue, such as by interassociating, intertangling, or grasping tissue, for extraction of the tissue from the treatment site. For example, the tissue manipulation element 172 of the manipulation tool 170 may be used to disrupt tissue and then capture the disrupted tissue for removal of the tissue from the treatment site. Alternatively, the tissue manipulation tool 170 may be used primarily as a disruption tool wherein a different tool is employed to remove the disrupted tissue from the treatment site, or the tissue manipulation tool 170 may be primarily used as an extractor or extraction tool that is employed to capture and remove residual nuclear and endplate material that has been disrupted by a different disruption tool.

The bristles or tines 178 are preferably made from biocompatible filaments. The tines 178 may vary in strength and flexibility. For example, the tines 178 may be soft, which is more conducive for engaging and capturing nucleus material, or hard, which is more conducive for disrupting nucleus tissue and disrupting and capturing endplate tissue. The tissue manipulation element 172 may also include a combination of soft and rigid tines. The density, placement, length and stiffness of the tines 178 can vary depending on such factors as the particular procedure being performed, the desired result of the procedure, the anatomical characteristics of the treatment site, the amount and type of tissue to be disrupted and/or extracted and the location of treatment site. For example, by configuring the tines 178 of the tissue manipulation element 172 to be dense, stiff and/or sharp, the tissue manipulation element 172 may be used to disrupt nuclear and endplate material. The tines 178 of the tissue manipulation element 172 may also be configured to engage and extract disrupted tissue from the treatment site. Additionally, the tines 178 may be in virtually any configuration. For example, the tines 178 may be in parallel rows and/or columns, they may be in a uniform spiral arrangement or they may be randomly spaced apart. Furthermore, the tines may be of a uniform size and shape or may vary in size and shape.

In one embodiment, the manipulation element may include two or more different types of tines in which each type of tine is particularly suited to disrupt or capture a particular type of tissue. For example, the manipulation element may include a first type of tines that are particularly well suited for disrupting disc tissue and a second set of tines that are particularly well suited for disrupting vertebral endplates. In one such embodiment, the first type of tines for disrupting disc tissue may be located on or at a distal end portion of the manipulation element and the second type of tines for disrupting endplates may be located on or at a proximal end portion of the manipulation element. In a further embodiment, the first and second type of tine may be randomly arranged on the tissue manipulation element, arranged in an alternating pattern, helical or screw-like pattern or intermixed, depending on the desired application.

In use, the tissue manipulation tool 170 is mounted onto and advanced over the guide member, through the cannula 38 and into the nucleus space 26 of vertebra 24. As the tissue manipulation element 172 is advanced over the distal end portion 34 of the guide member 30, it follows along the pre-defined path of the guide member 30. As the tissue manipulation tool 170 is translated back and forth along the guide member 30 and, optionally, rotated about the guide member 30 (as generally indicated by arrows 180 and 182) the tissue manipulation element 172 disrupts and captures tissue for removal. The tissue manipulation tool 170, with tissue attached thereto, is then retracted and removed from the intervertebral disc 24. The tissue manipulation tool 170, now outside of the patient may be cleaned and then reinserted into the patient to disrupt and capture more material. Alternatively, a new unused tissue manipulation tool can be inserted over the guide member 30 and into the nucleus space 26. The same procedure is repeated until lack of tissue on the tissue manipulation element indicates that the nucleus space 26 has been cleared of the desired amount of tissue.

FIGS. 43-52 illustrate another embodiment of a tissue manipulation tool 230 and a method of manufacturing such a tool. Referring to FIG. 43, similar to the manipulation tool 170, tissue manipulation tool 230 includes a tissue manipulation element or section 232 located at the distal end portion 234 of a pushing or elongated member 236, which may be any of the shafts described herein or any other suitable pushing member. The tissue manipulation element 232 includes a plurality of radiating brush-like elements, such as tines or bristles 238. Preferably, the tines 238 radiate from the tissue manipulation element 232 in a generally helical pattern. The tines 238 may be used to disrupt and/or extract tissue. The tissue manipulation element 232 may be flexible so that it is advanceable along a guide member 240 through a cannula 242 and into a treatment site. Preferably, the tissue manipulation element 232 is sufficiently flexible so that it may be inserted through a single access port and substantially reach all of the desired locations within the treatment site. Alternatively, the tissue manipulation element 232 may also be substantially rigid. Preferably, the components of the tissue manipulation tool 230 are made from radiopaque materials that are visible under fluoroscopy, or other imaging system, during advancement of the tool into the patient.

The manipulation tool 230 may also include a handle 244 that may be used to translate the manipulation tool 230 along the guide member 240 and rotate the manipulation tool 230 about the guide member 240. The handle 244 and the pushing member 236 may be of unitary construction or the handle 244 and pushing member 236 may be separate pieces that are attached to each other by, for example, adhesive bonding, welding or the like. The handle 244 is preferably generally ball shaped for easy gripping and has a passageway therethrough for the passage of the guide member 240.

The overall outer diameter of the tissue manipulation element 232 can vary in size depending on the particular application. For disrupting and/or removing tissue from an intervertebral disc, the outer diameter may be between about 0.16 inches (4 mm) and about 0.47 inches (12 mm). In one embodiment, the outer diameter is about 0.24 inches (6 mm). The length of the tissue manipulation element 232 may also vary depending on the particular application. For example, the length of the tissue manipulation element may be between about 0.20 inches (5 mm) and about 1.4 inches (35 mm). In one embodiment, the length is about 0.6 inches (15 mm).

Referring to FIG. 48, the tissue manipulation element 232 includes an internal support member 248 and at least one elongated member 250 mounted over the internal support member. The elongated member 250 includes a plurality of tines 238, which provides the brush-like appearance of the tissue manipulation element. The internal support member 248 is preferably a flexible tubular member, such as a spring coil, a hollow braided tube, laser-cut hypotube or the like. The internal support member 248 may be made from materials such as metal, metal alloys or a polymer. Preferably, the internal support member 248 is made from stainless steel, nitinol or titanium. Additionally, the material of the internal support member 248 may be radiopaque or a radiopaque impregnated material so that it is visible under fluoroscopy.

Referring to FIG. 44, the internal support member 248 preferably includes an outer surface 252 to which the elongated member 250 may be mounted. In one embodiment, the elongated member 250 is wound, preferably helically, around the outer surface 252 of the internal support member 248, as shown in FIG. 48. As explained in more detail below, the elongated member 250 may be attached and/or bonded to the internal support member 248.

Preferably, the inner surface (not shown) of the internal support member 248, which defines a passageway for receiving the guide member therethrough, is a smooth, flexible surface that assists in articulating the tissue manipulation element 232 over the guide member. The internal support member 248 preferably has an inner diameter that is slightly larger than the outer diameter of the guide member 240. For example, if the guide member 240 has an outer diameter of about 0.060 inch (1.5 mm), the inner diameter of the internal support member may be about 0.080 inch (2.0 mm). The outer diameter of the internal support member 248 may be between about 0.09 inch (2.25 mm) and about 0.2 inch (4.0 mm). However, the inner diameter of the internal support member 248 may be larger or smaller depending on the particular application. Preferably, the inner diameter is sufficiently large to accommodate the bending of the tissue manipulation element 232 along the guide member 240.

The internal support member 248 also provides a mechanical support that aids in preventing the helically wound elongated member(s) of the tissue manipulation element 232 from collapsing and/or binding onto guide member 240 as the tissue manipulation element 232 is articulated over the guide member 240 and/or rotational or tensile forces are applied to the tissue manipulation element 232. The internal support member 248 and the pushing member 236 may be of a single unitary construction or the internal support member 248 may be attached to the pushing member 236, by for example welding or adhesive bonding.

FIGS. 44 and 45 illustrate two embodiments of the internal support member 248a and 248b. In each of these embodiments, the internal support members 248a and 248b are formed from a wire or a ribbon, such as a stainless steel wire or flat ribbon, that has been wound into a generally helical coil. When a ribbon is utilized to form the coiled internal support member, the ribbon may provide a greater surface area onto which the elongated member may be attached. When a wire is utilized to form the coiled internal support member, the outer diameter of the wire is preferably between about 0.09 inch (2.25 mm) and about 0.2 inch (4.0 mm), other sizes may also be suitable. The wire or ribbon may be wound into a right-handed coiled internal support member 248a (FIG. 44) or a left-handed coiled internal support member 248b (FIG. 45).

Figure 56:
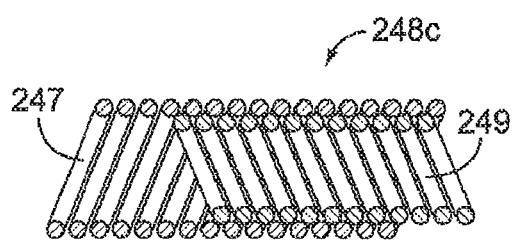
FIG. 56 is a partial cross-sectional view of one embodiment of an internal support members.

Additionally, the internal support member may be a single coil structure or a multi-layer coiled structure. FIG. 56 illustrates one example of a counter-wound dual layer coil internal support member 248c. The internal support member 248c includes an outer coil 247 and an inner coil 249. The outer coil 247 and inner coil 249 are preferably wound in opposite directions. In the illustrated embodiment, the outer coil 247 is wound in a right-hand fashion and the inner coil is wound in a left-hand fashion. Dual layer coiled internal support members with opposite wound inner and outer coils can provide greater torsional stiffness and enhanced response of torque transmission along the tissue manipulation element in either a clockwise or counter-clockwise rotation, which may be particularly helpful in procedures that require disruption and removal of tougher and stronger tissue. For example, a dual layered counter-wound coiled internal support member can enhance one to one torque transmission along the tissue manipulation element 232. In other words, the dual layered counter-wound configuration can enhance the transfer of torque from the proximal end of the internal support member to the distal end of the internal support member.

Figure 60:
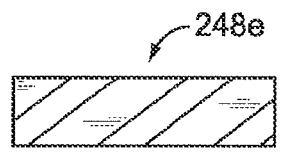
Figure 61:

FIGS. 60 and 61 illustrate alternative embodiments of the internal support member. In these embodiments, the internal support members 248d and 248e are braided hollow tubular members. The internal support members 248d and 248e may be multi-layer extruded tubular members that are reinforced with metal wire or ribbons to provide flexible, torqueable tubular members. The internal support members 248d and 248e may have a smooth inner wall that defines a passageway for receiving the guide member and provides smooth articulation over the guide member. The outer surface of each of the internal support members 248*d* and 248*e* may provide a support to which the elongated member can be mounted. The characteristics of the braided tubular members may be optimized for a particular application by varying the braid wire material and geometry, the braid pattern, and the polymer extrusion materials and thickness.

Figure 57:
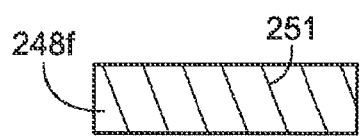
FIGS. 57-61 are side views of alternative embodiments of internal support members.
Figure 58:
Figure 59:
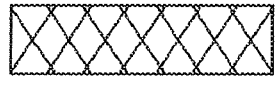

FIGS. 57-59 illustrate other alternative embodiments of the internal support member. In these embodiments, the internal support members 248*f*, 248*g* and 248*i* are flexible hypotubes made from a metal, such as stainless steel or nitinol, or any other suitable material. In FIG. 57, the internal support member 248*f* has a simple spiral cut pattern 251. In FIGS. 58 and 59, the internal support members 248*g* and 248*i* have more complex cut patterns 253 and 255. The cut patterns provide the internal support members 248*f*, 248*g* and 248*i* with sufficient flexibility to be translated over the guide member. The cut pattern may be cut in a manner that permits the transmission of torque through the hypotube in either a clockwise direction or counter clockwise direction. Preferably, the cut pattern permits transmission of torque in both directions. The hypotubes can be optimized for a particular application by varying the material, thickness and geometry of the hypotube and the cut patterns.

When the internal support member is constructed from a hypotube, the hypotube may provide both the pushing member and the internal support member of the tissue manipulation element. In such an embodiment, the distal end portion of the hypotube forms the internal support member and the proximal end portion forms the pushing member. The distal end portion has a cut pattern that makes the distal end portion suitable for use as the internal support member. The proximal end portion may be solid without any cut patterns or includes the same or a different cut pattern than the distal end portion.

Turning now to the elongated member 250 that is mounted onto the internal member 248. The elongated member 250 may be an elongated ribbon, wire or strip of material that, preferably, has a larger length than its width. Additionally, when the elongated member 250 is a ribbon or a strip of material, the thickness of the elongated member may be thin and, preferably, significantly less than the elongated member's width. The elongated member 250 is preferably made of materials that are biocompatible and suitable for at least temporary exposure within the body. The materials also are preferably capable of withstanding forces associated with tissue disruption and extraction. Such materials may include metals, metal alloys, polymers or any other suitable material or combination of materials. For example, the materials of the elongated member may include stainless steel, nitinol, titanium, PEEK, polyethylene or nylons. Preferably, the material is radiopaque so that it is visible under fluoroscopy. When the elongated member 250 is made from a polymer, its visibility under fluoroscopy may be enhanced by impregnating it with barium sulfate or including radiopaque markers, at least at the proximal and distal ends of the elongated member.

Referring to FIG. 46, the elongated member 250 includes a main body 254 and a plurality of projections, such as tines 238, extending from one or both of the edges of the main body 254. The tines 238 extend at an angle from the plane of the main body 254. The tines 238 and the main body 254 may be of a single unitary construction or they may be separate pieces that are assembly together. For example, the main body 254 may be a polymer material to which metal tines 238 are attached during the manufacturing process. Alternatively, the main body 254 may be a metal material to which polymer tines 238 are attached. In another embodiment, wherein the tines 238 and the main body 254 are of a unitary construction, the tines 238 and main body 254 may be formed from a strip of material by stamping, punching or cutting out portions of the material along one or both edges of the material. The elongated member's main body 254 and tines 238 may also be formed by lithography or molding.

Figure 52:
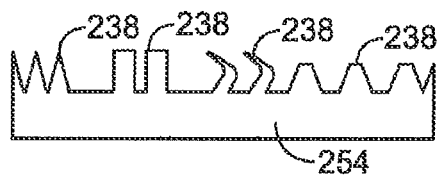
FIG. 52 is a top view of an elongated member showing exemplary tine configurations.

The tines 238 can have virtually any shape, such as triangular, rectangular, sawtooth, trapezoidal or other desired shape. The tines 238 may also be beveled or serrated. Some of non-limiting exemplary shapes of the tines 238 are illustrated in FIG. 52. Additionally, the plurality of tines 238 along the length of an elongated member 250 may be uniform in size and shape, or the shape and size of the tines 238 may vary along the length of the elongated member 250. Also, the tines 238 and the main body 254 may include features that reduce stress that is applied to the elongated member 250 during tissue disruption and/or extraction. Such stress reduction features may include stress-relieved corners and fillets at the junction between the tine 238 and the main body 254 of the elongated member 250.

FIGS. 46 and 47 illustrate one embodiment of a method of forming the elongated member 250. FIG. 46 illustrates an elongated member 250 in which the tines 238 are initially in the same plane as the main body 254. Such a structure may be constructed, for example, by stamping, punching or cutting out portions along the edges of a strip of material to form a main body 254 and a plurality of tines 238. As illustrated in FIGS. 47 and 50, the tines 238 are then bent or otherwise deformed so that the tines 238 extend at an angle from the plane of the main body 254. The plurality of tines 238 may all be bent at the same angle, or the tines 238 may be bent at varying angles. Referring to FIG. 51, optionally, the tines 238 also may be compoundedly bent at two or more angles. The shape, size, angle of extension, bend angle and material of the tines may be varied to optimize the tines for cutting and/or capturing a particular type or types of tissue.

After the elongated member 250 has been formed, it is mounted to the internal support member 248. Turning to FIG. 46, in one embodiment, the elongated member 250 is wound or wrapped around the internal support member 248 in a helical fashion. When a coiled internal support member is utilized, the elongated member may be counter-wound with respect to the coiled internal support member. The counter winding of the elongated member increases structural integrity of the tissue manipulation element and may prevent undesired mechanical interactions. For example, the counter winding can prevent stretching or enlargement of the tissue manipulation element when exposed to rotational forces. The elongated member 250 is wound so that the tines 238 project radially outward from the internal support member 248 so as to form a brush-like structure. Preferably, the elongated member 250 is tightly wound around the internal support member 248. The pitch of the winding may be open or closed and the pitch may vary along the length of the internal support member 248 as necessary to provide more or less flexibility along the length of the tissue manipulation element being formed. The distance or pitch between each winding of tines 238 (designated as 256 in FIGS. 43 and 48) of the tissue manipulation element 232 may be controlled by the pitch of the helically wound elongated member 250 and the width of the elongated member 250.

To help ensure that the elongated member 250 does not unwind or detach from the internal support member 248, the elongated member 250 may be coupled to the internal support member 248 by a mechanical coupling or otherwise. Attachment of the elongated member to the internal support member also helps the elongated member from expanding, stretching and/or buckling when the tissue manipulation element is exposed to torsional or axial forces. For example, the elongate member 250 may be secured to the internal support member 248 by a bonding agent, soldering, laser welding, RF welding or the like. Alternatively or additionally, an additional attachment element may be used to secure the elongated member 250 to the internal support member 248. For example, a wire member may be coiled around the elongated member 250 and between the tines 238 to secure the elongated member 250 to the internal support member 248. In yet another alternative, coupling may be achieved by plastic deformation of the elongated member 250. For example, the elongated member 250 may be wound onto the internal support member 248 under tension so that the elongated member 248 takes a substantially identical shape as the internal support member 248, much like when a wire coil is wound under tension on a mandrel. In yet a further coupling alternative, when the elongated member 250 is made from a shape memory metal and a polymer, an appropriate heating protocol may be used to substantially conform the shape of the wound elongated member 250 to shape of the internal support member 248.

The proximal end portion 258 and the distal end portion 260 of the tissue manipulation element 232 may encounter different forces and stresses during use. Thus, the proximal end portion 258 and the distal end portion 260 may be coupled to the internal support member 248 in different manners. For example, the shear forces encountered between the proximal end portions of the internal support member and the elongated member may be higher than the shearing forces between the distal end portions of the two. Thus, the elongated member's proximal end portion and distal end portion each may be coupled to the internal support member in a manner that is particularly well suited for withstanding the unique forces and stresses that each end portion may encounter.

The tissue manipulation element 232 may include a single elongated member or a plurality of elongated members mounted onto the internal support member 248. Referring to FIG. 49, a second elongated member 250a may be wound around the internal support member 248. The second and other subsequent elongated members 250a may be wound so that it overlaps the immediate preceding elongated member 250 or it may be wound so that it is located in between the windings of the preceding elongated member 250 or a combination of both. The second and other subsequent elongated members 250a may be used to increase the density of the tines 238 of the tissue manipulation element 232, vary the height of the tines 238 or vary the angle and direction of the tines 238. Thus, the second and subsequent elongated members 250a may include tines 238 that have shapes and sizes that are different from those of the previous mounted elongated member(s) 250 and/or tines that extend at a different angle and/or direction than those of the previous elongated member(s) 250.

Figure 53:
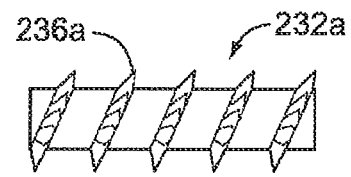
FIGS. 53-55 are side views of alternative embodiments of tissue manipulation elements.
Figure 54:
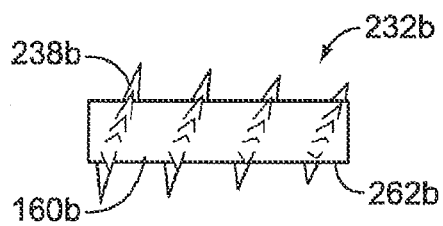
Figure 55:
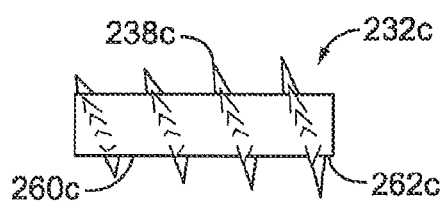

FIGS. 53-55 illustrate some exemplary embodiments of tissue manipulation elements 232a, 232b and 232c having tines 238 of different configurations. All of the embodiment shown in these figures may be tissue manipulation elements that include a single elongated member or multiple elongated members. FIG. 53 shows a tissue manipulation element 232a in which all of the tines 236a have a substantially uniform height. FIG. 54 illustrates a tissue manipulation element 232b in which the height of the tines 238b located nearer the distal end portion 260b of the tissue manipulation element 232b are larger than the height of the tines 238b located nearer the proximal end portion 262b. FIG. 55 illustrates a tissue manipulation element 232c in which the height of the tines 238c located nearer the proximal end portion 262c of the tissue manipulation element 232c are larger then the height of the tines 238c nearer the distal end portion 260c. Varying the height along the length of the tissue manipulation member may be useful for penetrating and treating wedge shaped treatment sites. For example, a tissue manipulation element that has tines which are smaller at the proximal end portion and larger at the distal end portion may be effective in treating a lordodic disc space. The varying height of the tines 238 may be accomplished by varying the height of the tines along an individual elongated member 250 or by varying the height of the tines between elongated members.

FIG. 62 illustrates another embodiment of a tissue manipulation tool 266. Tissue manipulation tool 266 includes an elongated tubular member 267 including a distal or leading end section 268, an intermediate or mid-section 270 and a proximal or trailing end section 272. Elongated tubular member 267 also includes a passageway or lumen 269 (shown in FIG. 65) passing therethrough. A guide member, such as a guide wire or any of the guide members disclosed herein, may be received into the passageway of tubular member 267 for translation of the tissue manipulation tool 266 over the guide member. In one embodiment, tissue manipulation tool 266 may be deployed over a guide member having a distal looped configuration, such as those shown in FIGS. 9, 9A and 63.

Turning back to FIG. 62, at least intermediate section 270 of tissue manipulation tool 266 includes a tissue manipulation element 274. In the illustrated embodiment, the tissue manipulation element 274 comprises a plurality of tines 276 helically arranged around mid-section 270 of elongated tubular member 267. Tines 276 may be any of the tines or bristles described herein and may be in any of the various arrangements described herein. Furthermore, the manipulation element 274 may be any of the disruption or capturing elements disclosed herein. For example, tissue manipulation element 274 may include disruption elements that may be, but are not limited to, blades, bladed edges, wires, etc. In the embodiment shown, the manipulation elements are not located on the proximal and distal end portions 268,272 of tissue manipulation tool 266. In other embodiments, however, the proximal and/or distal end portions 268 and 272 may also include tissue manipulation elements. The length of sections 268, 270 and 272 may vary depending on a varied of factors, such as on the desire procedure, the location of the procedure, the type of material to be removed and/or the method of delivering the tool (e.g., manual or mechanized).

FIGS. 63-66 illustrate various devices and methods that may be used in conjunction with tissue manipulation tool 266 to deliver tissue manipulation tool 266 into an intervertebral disc space. Turning to FIG. 63, a distal end portion 278 of delivery cannula 280 may be inserted through an access opening 281 through the annulus fibrosis 282 of an intervertebral disc 283 and into the nuclear disc space 284. In the illustrated embodiment, delivery cannula 280 is at least a dual lumen cannula having a first lumen 286 and a second lumen 288 (both of which are shown in phantom). The methods described herein may also employ a single lumen cannula.

A guide member 290 is movably located within the lumens 286, 288 of cannula 280. Guide member 290 includes a first section 292 located within lumen 286 of the delivery cannula 280 and a second section 294 extending from lumen 286 and returning to into lumen to 288. Guide member 290 also includes a third section 296 extending through lumen 288. When delivery cannula 280 is inserted into the intervertebral disc 283, the second section 294 of guide member 290 may be closely adjacent or tightly held (for example, via tension) to the distal end portion 278 of delivery cannula 280 for ease of insertion of cannula 280 and guide member 290 into the intervertebral disc 283 and in one embodiment into the nuclear disc space 284.

After delivery cannula 280 has been placed in the desired position within intervertebral disc 283, guide member 290 may be moved distally through cannula 280 so that second section 294 of guide member 290 extends beyond the distal end of the cannula and defines a continuous loop in the distal end portion of guide member 290. In FIG. 63, second section 294a shown in phantom is the continuous loop defined by second section 294, after guide member 290 has been deployed. The continuous loop defined by guide member 290 may be formed in several different manners. In one example of deploying guide member 290, first section 292 of guide member 290 is advanced distally in the direction of arrow 289 through first lumen 286 of delivery cannula 280 while third section 296 of guide member 290 is held stationary. Advancement of first section 292 results in second section 294 defining a loop within intervertebral disc 283. In another embodiment, first and third sections 292 and 296 of guide member 290 are advanced distally simultaneously or sequentially so that second section 294 defines a continuous loop within intervertebral disc 283.

Second section 294 of guide member 290 may include one or more flex regions or points therealong. The flex regions or points are areas of the guide member that are designed to flex when under stress or relieved of stress. One or more flex regions or points along the guide member may assist in forming the desired shape of the continuous loop during deployment of the guide member.

Referring now to FIG. 64, after guide member 290 has been deployed within intervertebral disc 283 and the distal end portion of guide member 290 has been formed into the desired continuous loop (as shown in FIG. 63), tissue manipulation tool 266 is advanced distally over guide member 290 in the direction of arrow 291 and into the intervertebral disc space. In one embodiment, guide member 290 is received into the passageway 269 (shown in FIG. 65) of tissue manipulation tool 266. Tissue manipulation tool 266 is advanced over first section 292 of guide member 290 and through first lumen 286, over the second section 294 of guide member 290 defining the continuous looped distal end of guide member 290, and then over third section 296 of guide member 290 and returning through second lumen 288 of cannula 280. As the tissue manipulation element 274 passes through the intervertebral disc 283, tines 276 contact and manipulate the disc tissue and/or endplate tissue. For example, tissue manipulation element 274 disrupts (e.g. cuts, tears, scrapes or abrades) the tissue, removes or partially removes the tissue (e.g. by capturing tissue) and/or both disrupts and removes tissue. In one embodiment, the second lumen 288 is sufficiently large to accommodate passage of the tissue manipulation tool having tissue attached thereto. In such embodiments, the second lumen 288 may, but is not necessarily, larger than the first lumen 286. As the tissue manipulation element 274 passes through the intervertebral disc 283, tines 276 contact and manipulate the disc tissue and/or endplate tissue.

Figures 65, 66:
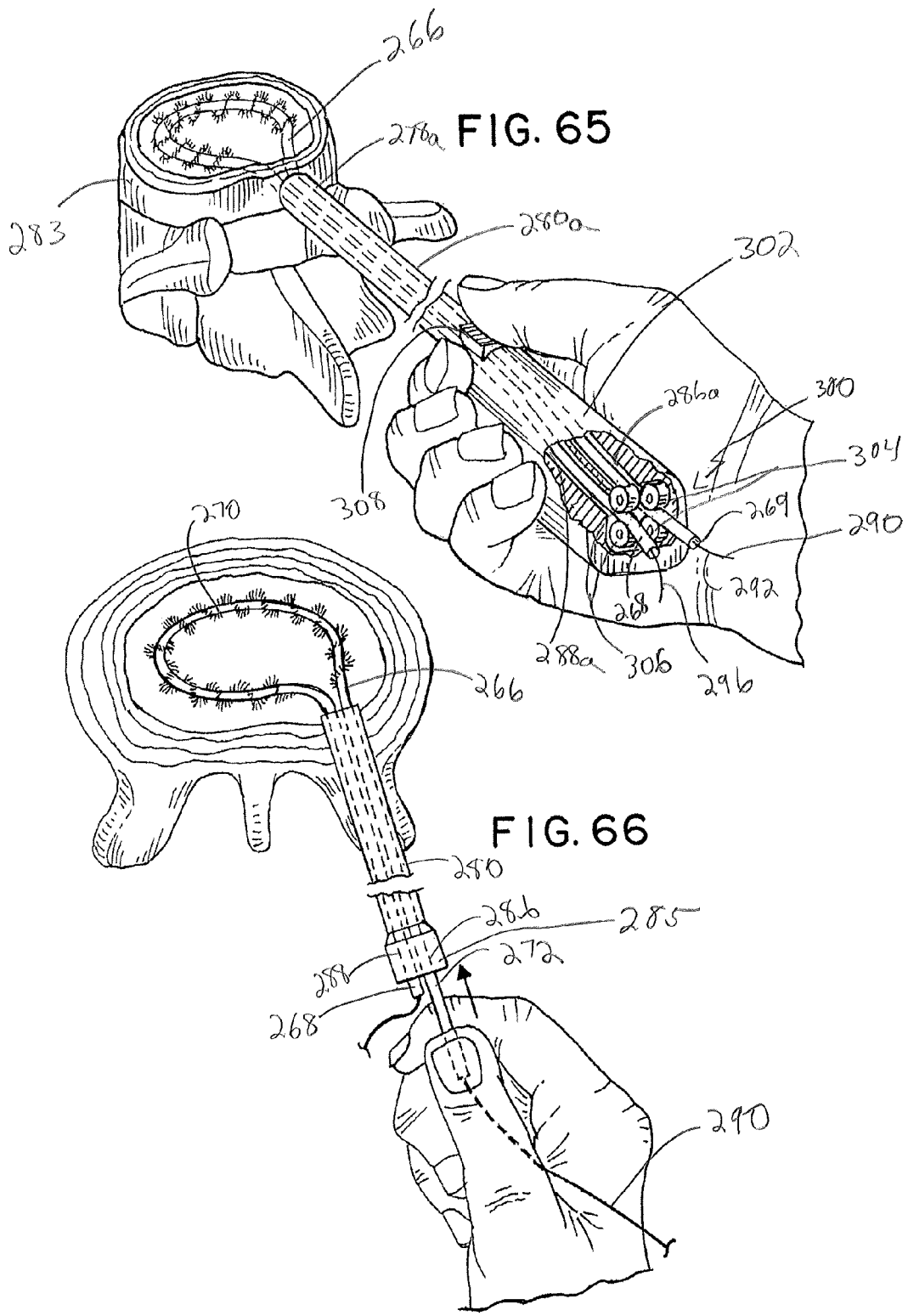
FIG. 65 is a perspective view of one embodiment of a delivery system that may be employed to deliver a tissue manipulation tool.
FIG. 66 is a cross-sectional view of an intervertebral disc having a tissue manipulation tool deployed therein and showing one method of advancing the tissue manipulation tool over the guide member.

FIGS. 65 and 66 illustrate different methods of advancing tissue manipulation tool 266 over guide member 290. In each of these figures, tissue manipulation tool 266 is shown at the point of mid-delivery of the below described methods.

Referring to FIG. 65, distal end portion 278a of delivery cannula 280a has been inserted into intervertebral disc 283 and guide member 290 has already been deployed so that the distal end of guide member 290 defines a continuous loop similar to that which is shown in FIG. 63.

Similar to delivery cannula 280 shown in FIG. 63, delivery cannula 280a is a dual lumen cannula including first lumen 286a and second lumen 288a. Delivery cannula 280a may further include an optional drive or feed mechanism 300 associated therewith. Drive mechanism 300 drives or feeds tissue manipulation tool 266 over guide member 290. In the illustrated embodiment, drive mechanism 300 includes a pinch roller assembly located in a proximal end 302 of delivery cannula 280a. The pinch roller assembly includes a first pair of opposed rollers 304 and a second pair of opposed rollers 306, which may be controlled by switch 308. First pair of pinch rollers 304 extends into or is located adjacent to the proximal end of lumen 286a of cannula 280a, and second pair of opposed rollers 306 extends into or is located adjacent to the proximal end of second lumen 288a. First section 292 of guide member 290 is located between first pair of pinching rollers 304 and extends through lumen 286a of cannula 280a. Third section 296 of guide member 290 is located between second pair of pinching rollers 306 and extends through lumen 288a of cannula 280a.

To advance tissue manipulation tool 266 along guide member 290, first section 292 of guide member 290 is received into passageway 269 of tissue manipulation tool 266 and tissue manipulation tool 266 is advanced along guide member 290. Distal or leading end portion 268 of tissue manipulation tool 266 is feed between the first pair of pinching rollers 304. Pinching rollers 304, which are rotating in the opposite direction relative to each other, contact leading end 268 of tissue manipulation tool 266 to feed the tissue manipulation tool into first lumen 286a of cannula 280a and along first section 292 of guide member 290. Pinching rollers 304 preferably are powered by electrical or manual drive system. As tissue manipulation tool 266 is feed into lumen 286a and advanced along guide member 290, mid-section 270 and trailing section 272 pass between and come into contact with rollers 304, which continues to advance tissue manipulation tool 266 along guide member 290.

Driven along guide member 290 by the first pair of pinching roller 304, leading end 268 of tissue manipulation tool 266, with mid-section 270 and trailing section 272 following therebehind, translate over first section 292 of guide member 290, out of the first lumen 286a of cannula 280a, along the continuous loop defined by the distal end portion of guide member 290 and into the second lumen 288a of cannula 280a. Leading section 268 of tissue manipulation tool 266 is translated over third section 296 of guide member 290, through second lumen 288a of cannula and between the second pair of pinching rollers 306, which are optionally powered by an electrical or manual drive system. In one embodiment, the length of tissue manipulation tool 266 is such that as leading end 268 comes into contact with the second pair of rollers 306, trailing end 272 is disengaging the first pair of rollers 304. The second pair of pinching rollers 306, which are rotating in opposite directions relative to one another, contact leading end 268 of tissue manipulation tool 266 to pull the manipulation tool along guide member 290 and out of second lumen 288a of cannula 280a. The above-described process may then be repeated with additional tissue manipulation tools. The manipulation tool may be manipulated by moving (e.g., by advancing, retracting or rotating) the cannula 302, by moving (e.g., advancing and retracting) the leading or trailing ends of the guide member, or by sliding the tool back and forth over the guide member.

Turning now to FIG. 66, in this embodiment, tissue manipulation tool 266 is translated over guide member 290 by hand. For example, the first section 292 of guide member 290 may be received into a passageway of tissue manipulation tool 266 so that the tissue manipulation tool may be advanced over guide member 290. A user may grasp leading section 268 of tissue manipulation tool 266 and push the tissue manipulation tool along the first section 292 of guide member 290 and into the first lumen 286 of cannula 280. The user may then grasp trailing end 272 of tissue manipulation tool 266 and continue to advance mid-section 270 and trailing end 272 of tissue manipulation tool 266 through first lumen 286 and out of the distal end portion 278 of cannula 280. Tissue manipulation tool 266 follows along guide member 290 and along the continuous loop defined by the distal end portion of the guide member. As tissue manipulation tool 266 is advanced along guide member 290, the leading end portion 268 is advanced into and through the second lumen 288 of cannula 280 and out of proximal end 285 of cannula 280. When leading end 268 extends out of proximal end 285 of cannula 280, the user may grasp leading end 268 and pull it to pull tissue manipulation tool 266 along the rest of guide member 290 and out of the second lumen 288 of cannula 280. The above-described process may then be repeated with additional tissue manipulation tools.

Figure 37:
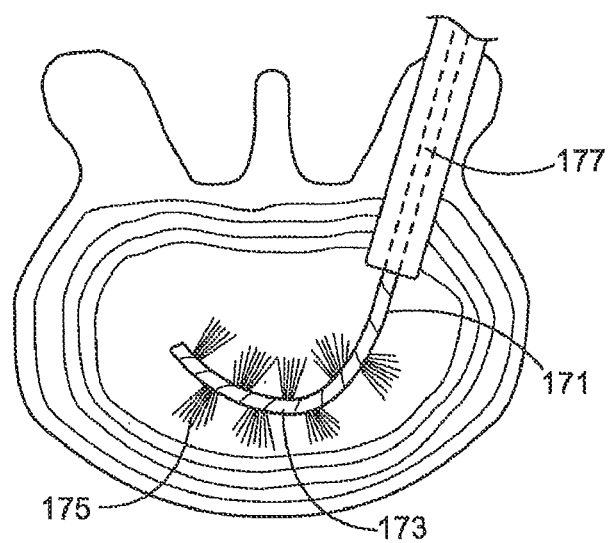
FIG. 37 is a top view of another embodiment of a tissue manipulation tool constructed in accordance with the present disclosure and shown deployed within a disc space.

FIG. 37 illustrates another embodiment of a tissue manipulation tool. The tissue manipulation tool may include a pushing member 171, such as a rod, ribbon or wire, that has a tissue manipulator or manipulation element 173 located at the distal end of the elongated member. In the embodiment shown, the tissue manipulation element 173 includes tines 175. The tissue manipulation element 173 may be substantially similar to the tissue manipulation elements 172 and 232 described above. The elongated member 171 may be constructed of a shape memory material that is pre-set to a desired shape. When constructed from a shape memory material, the elongated member 171 may be straightened for deployment through a cannula 177 and then returned to its pre-set shape upon exiting the cannula. In one embodiment, the elongated element 171 may be a twisted wire, such as a twisted nitinol wire.

Figure 38:
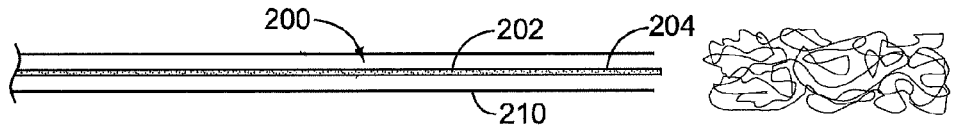
FIG. 38 is a side view of another embodiment of a tissue manipulation tool constructed in accordance with present disclosure.
Figure 39:
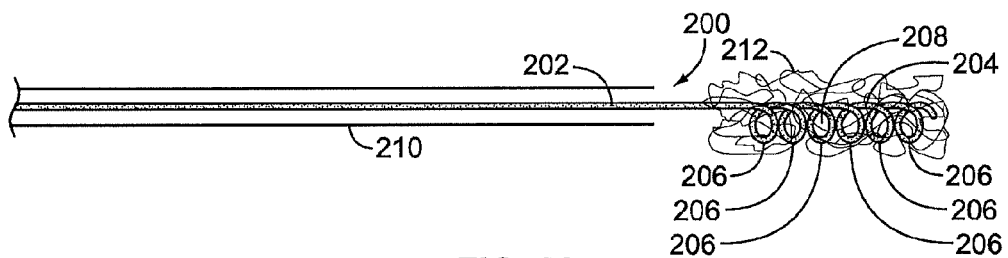
FIG. 39 is a side view of the tissue manipulation tool of FIG. 38 shown in the deployed configuration.
Figure 40:
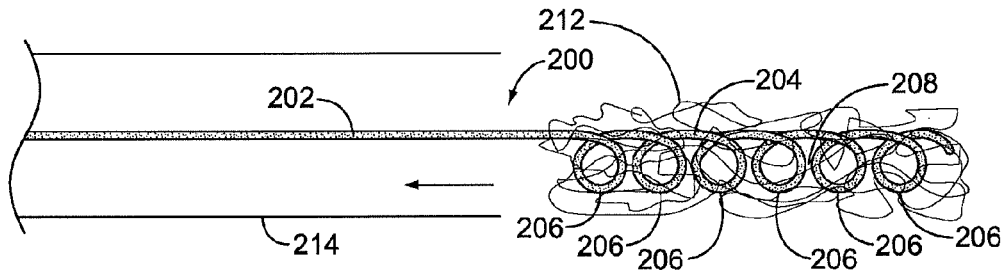
FIG. 40 is a side view of the tissue manipulation tool of FIG. 38 shown being retracted into a cannula.

FIGS. 38-40 illustrate another embodiment of a tissue manipulation tool that may be used as a tissue extraction tool. Referring to FIG. 39, the tissue extraction tool 200 includes an elongated element 202 having a generally helically shaped distal end portion 204. The generally helically shaped distal end portion 204 includes a plurality of coils 206. The coils 206 generally define an inner space or volume 208. Preferably, at least the helically shaped distal end portion 204 of the elongated element 202 is made from a shape memory material, for example nitinol, so that at least the distal end portion 204 of the elongated element 202 can be transformed or constrained into a generally linear or straight configuration for deployment through a delivery cannula 210, as shown in FIG. 38. Referring back to FIG. 39, as the distal end portion 204 of the tissue extraction tool 200 exits the distal end of the cannula 210, it transitions into its helical shape and travels through the tissue 212 to be removed. The distal end portion 204 may be inserted into the tissue 212 in a linear or rotational translation. The tissue 212 becomes ensnared, entangled or otherwise entrapped in the inner space 208 generally defined by the coils 206. It will be understood that the extraction tool 200 does not necessarily need to be straightened for insertion into the tissue and that the extraction tool can be inserted into tissue in its helical configuration.

Turning to FIG. 40, after the helically shaped distal end portion 204 is in the desired position, the delivery cannula 210 may be removed and a second larger cannula 214 may be placed over the extraction tool 200. Preferably, the size of the inner diameter of the internal lumen of the second cannula 214 is about the same size or slightly larger than the outer diameter defined by the coils 206 of the helical distal end portion 204 of the extraction tool 200. After the second cannula 214 is in the desired location, the tissue extraction tool 200 is retracted into the second larger cannula 214. As the tissue extraction tool 200 is retracted, the pitch of each coil 206 slightly tightens, reducing the inner space 208 generally defined by the coils 208, thereby trapping the tissue in the inner space 208 and between the coils 206. The extraction tool 200 with the tissue 212 trapped within the coils 206 is then retracted into the second delivery cannula 214 to remove the tissue 212 from the treatment site.

If desired, a secondary element may be utilized to assist facilitating the tightening of the coils 206 and the collapse of the inner space 208. For example, the secondary element may be an elongated stop mechanism that tracks or slides along the extraction tool 200 and contacts one or more the distal most coils or the distal tip of the extraction tool 200. The stop mechanism may contact the distal most coils and act as a stop that maintains the distal most coils in a stationary position. With the distal most coils held in a stationary position, the extraction tool 206 is retracted, causing the coils 206 to tighten, which reduces the inner space 208 generally defined each coil.

In alternative embodiment, the extraction tool 200 can be guided by a guide member into the tissue. A guide member, which may be any of the guide members discussed above, is inserted into the tissue. The distal end portion 204 of the extraction tool 200 may then be slideably attached to the guide member so that the extraction tool 200 can be advanced or tracked along the guide member. For example, the distal end portion 204 of the extraction tool 200 may include an attachment member, such as a collet or tube or ringlet into which the guide member can be inserted.

Figure 41:
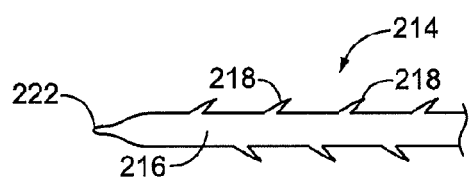
FIG. 41 is a side view of yet another embodiment of a tissue manipulation tool constructed in accordance with the present disclosure.
Figure 42:
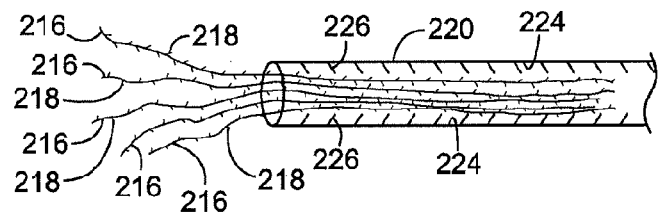
FIG. 42 is a side view of the tissue extraction tool of FIG. 41 and one embodiment of a deployment cannula.

FIGS. 41 and 42 illustrate yet another embodiment of an extraction tool 214. Referring to FIG. 40, the extraction tool 214 can include an elongated member 216 that has a plurality of projections, such as barbs 218, extending radially outwardly from the elongated member 216. The elongated member 216 can be, for example, a rod, wire, or ribbon. Preferably the elongated member 216 is made from a biocompatible material. The elongated member may be made from a metal, such as stainless steel, or a metal alloy, such nitinol, or a biocompatible polymer. The barbs 218 may extend from the elongated member 216 in virtually any pattern, for example, spiral, columns and rows or randomly. Preferably, the barbs 218 are "one way" barbs that extend at an angle relative to the elongated member 216 and in a generally proximal direction. Additionally, the barbs 218 may have any variety of configurations, including for example, sharp, blunt, straight, hook shaped, zig-zagged, etc.

Turning to FIG. 42, when in use, one or more elongated members 216 are inserted into the tissue to be removed through a cannula 220. Preferably, the angle and direction of extension of the barbs 218 are such that the elongated members 216 travel through the tissue relatively easily. In the embodiment shown, the barbs 218 are "one way" barbs that extend in a proximal direction, which is also in a direction that is opposite the direction of insertion of the elongated member into the tissue. Because of the direction of the barb's extension, the elongated members 216 and barbs 218 may be inserted into the tissue with minimal resistance. Additionally, as shown in FIG. 41, the distal tip 222 of the elongated member 216 may be pointed to penetrate through tissue. Also, rigidity of the distal tip 222 may be configured so that the tip is suitable for penetration into one type of tissue but unable to penetrate through a second type of tissue. For example, the distal tip 222 may be configured to penetrate through nucleus tissue, but not through annulus tissue.

After the elongated members 216 have been inserted into the tissue a desired amount, the elongated members 216 are retracted back into the cannula 220. As the elongated members 216 are being retracted, the "one way" barbs 218 contact the tissue and entangle, ensnare, hook or otherwise capture the tissue. The elongated members 216, with the tissue captured by the barbs 218, continue to be retracted into the cannula 220 to remove tissue from the treatment site.

After the elongated members 216 have been retracted into the cannula 220, the elongated members 216 may be removed from the cannula 220 and a new, unused set of elongated members can be inserted through the cannula 220 into the treatment site to retrieve further tissue. Alternatively, the cannula 220 can include a barb cleaning mechanism. In the illustrated embodiment, the inner wall 224 of the deployment cannula 220 includes a plurality of cleaning projections, such as barbs 226. The cleaning barbs 226 may also be "one way" barbs that extend from the inner wall 224 at an angle and in the same direction as the barbs 218 of the elongated members 216. The cleaning barbs 226 may also extend in any other suitable direction, such as generally perpendicular to the inner wall of the cannula, and may have any configuration. Because the cleaning barbs 226 extend in the same direction as the barbs 218 of the elongated members 216, the elongated members 216, having tissue attached to the barbs 218, are retractable into the cannula 220 with minimal resistance.

After the elongated members 216 have been retracted into the cannula 220, the elongated members 216 are then again advanced out of the cannula 220. As the elongated members 216 are advanced out of the cannula 220, the cleaning barbs 226 contact the tissue associated with the barbs 218 of the elongated members 216 and strip, clean or otherwise remove the tissue from the barbs 218 of the elongated members 216. Thus, the cleaned elongated members 216 are inserted back into the treatment site to capture and remove additional tissue. The elongated members 216 can be repeatedly advanced out of and retracted into the cannula 220 to continually remove tissue from the treatment site.

The cutting, scraping and extraction tools described herein can be used in conjunction with each other to perform discectomy procedures. Alternatively, each tool can be used separately in any procedure for its individual purpose. Additionally, when used in conjunction with one another, the tools can be deployed over the same guide member, or different guide members, each having a different configuration, can be used to deploy each of the tools.

Additionally, the discectomy tools described herein can be supplied in a kit. The kit can include one or more tissue manipulation tools, such as the above-described cutting tools, scraping tools and tissue extraction tools. The kit can also include one or more guide members. Optionally, the kit can also include a working cannula for deploying the guide member and discectomy tools. In one embodiment, the kit can include a sterilized package or tray containing one of more guide members and one of more the above mentioned manipulation tools as well as other elements that can be used in combination with the discectomy tools.

FIG. 67 illustrated one embodiment of an endplate preparation tool 310 inserted into an intervertebral disc space 314 between adjacent vertebral bodies 311 and 313. In this embodiment, tool 310 is delivered into disc space 314 through a delivery cannula 312. Tool 310 may be used to disrupt (including by abrading) tissue of endplates 316 and 318 which is adjacent to disc space 314. For example, endplate preparation tool 310 may be used to scrape or puncture the endplates to induce bleeding thereof. Furthermore, endplate preparation tool 310 may be inserted into the disc space 314 after disc tissue has been removed or may be inserted into a disc space that contains disc tissue.

Endplate preparation tool 310 may comprise an elongated member such as a wire or ribbon, having a proximal end portion 320 and a distal end portion 322. Distal end 322 of tool 310 has a shape and construction that is suitable for disrupting tissue of the endplates 316 and 318. In one embodiment, distal end portion 322 includes a pointed terminal end that may be used to puncture endplates 316 and 318. In another embodiment, distal end 322 includes a blade or bladed edge. The blade may be a straight blade or include a teeth-like profile that may be used to scrape endplates 316 and 318.

Tool 310 is preferably, but not necessary, made of a strong, rigid material, such as a metal or metal alloy or a strong, rigid polymer material. In one embodiment, tool 310 is comprised of a shape memory material, such as a shape memory alloy, for example Nitinol.

In one embodiment, distal end portion 322 of tool 310 has an initial or curved configuration, such as the curved configuration shown in FIG. 67. The curved distal end portion 322 may be restrained in a substantially linear configuration for passage through delivery cannula 312. For example, when tool 310 is inserted into cannula 312, the inner wall 324 of cannula 312 forming lumen 326 restrains distal end portion 322 of tool 310 in a substantially straight or linear configuration for passage through lumen 326.

Distal end portion 322 is advanced through lumen 326 and out of opening 328 in the distal end portion 330 of cannula 312. In the illustrated embodiment, the cannula 312 includes a side opening 328. In alternative embodiments, cannula 312 may include a distal end opening. When distal end portion 322 extends from opening 328 of cannula 312, distal end portion 322 substantially returns to its initial curved configuration. Tool 310 or cannula 312 may be maneuvered or moved relative to each other and/or relative to the anatomical structures of disc space 314 to disrupt the tissue of endplates 316 and 318. The distal end may be shapted or include additional features, such as bristles or the like to assist in the disruption. Additionally, cannula 312 may be rotated as needed to allow tool 310 to contact both endplates 316 and 318.

Although the present invention is described in light of the illustrated embodiments, it is understood that this for the purposes illustration and not limitation. Other applications, modifications or use of the support or distraction device may be made without departing for the scope of this invention, as set forth in the claims now or hereafter filed.

What is claimed is:

1. A tissue manipulation system for manipulating tissue in or adjacent to an intervertebral disc space, the system comprising:

a deployment cannula having a proximal end portion, a distal end portion and at least one internal lumen;

a guide member movable within said at least one internal lumen of the cannula and out of the distal end portion of the cannula to define a substantially continuous loop wherein the guide member extends from and returns into the at least one lumen; and at least one tissue manipulator having a leading end and a trailing end and comprising one or more of a blade including a cutting edge for cutting tissue, a tissue scraper including a scraping edge for scraping tissue and/or a tissue extractor including a tissue capturing structure for capturing and removing tissue from the intervertebral disc space, the at least one tissue manipulator being movable within said at least one internal lumen of the cannula, the at least one tissue manipulator having a passageway for receiving the guide member such that both the leading and trailing ends of the at least one tissue manipulator are advanceable over the guide member, first out of the distal end portion of the cannula and then around the substantially continuous loop defined by the guide member and returning again into the at least one lumen.

2. The system of claim 1 in which the guide member is a guide wire.

3. The system of claim 1 in which the at least one tissue manipulator is adapted to disrupt disc tissue.

4. The system of claim 1 in which the at least one tissue manipulator is adapted to disrupt vertebral endplates.

5. The system of claim 1 in which the at least one tissue manipulator has a first portion adapted to disrupt disc tissue and a second portion adapted to disrupt vertebral endplates.

6. The system of claim 1 in which the at least one tissue manipulator comprises an elongated tubular member including a proximal end section defining the trailing end of the manipulator, a distal end section defining the leading end of the manipulator and a mid-section therebetween, wherein one or more tissue disruption elements are associated with the mid-section.

7. The system of claim 6 in which the proximal end section and the distal end section of the elongated tubular member are free of tissue disruption elements.

8. The system of claim 1 in which the substantially continuous loop has a substantially circular, elliptical or oval shape.

9. The system of claim 1 in which the at least one tissue manipulator is adapted to capture and remove tissue from the intervertebral disc space.

10. The system of claim 1 in which the at least one tissue manipulator includes a first tissue manipulator adapted to disrupt disc tissue, a second tissue manipulator adapted to disrupt vertebral endplates and a third tissue manipulator adapted to capture and remove tissue from the intervertebral disc space.

11. The system of claim 1 in which the at least one tissue manipulator is adapted to disrupt disc tissue, disrupt vertebral endplates and capture and remove tissue from the intervertebral disc space.

12. The system of claim 1, in which the cannula includes a first lumen and a second lumen, wherein the substantially continuous loop defined by the guide member extends from the first lumen and returns into the second lumen and both the leading and trailing ends of the at least one tissue manipulator are advancable from the first lumen, around the loop, and returning into the second lumen.

13. A tissue manipulation system for manipulating tissue in or adjacent to an intervertebral disc space, the system comprising:
a deployment cannula having a proximal end portion, a distal end portion and at least one internal lumen;
a guide member movable within said at least one internal lumen of the cannula and out of the distal end portion of the cannula to define a substantially continuous loop wherein the guide member extends from and returns into the at least one lumen; and
at least one tissue manipulator comprising one or more of a blade including a cutting edge for cutting tissue, a tissue scraper including a scraping edge for scraping tissue and/or a tissue extractor including a tissue capturing structure for capturing and removing tissue from the intervertebral disc space, the at least one tissue manipulator being movable within said at least one internal lumen of the cannula, the at least one tissue manipulator having a passageway for receiving the guide member such that the at least one tissue manipulator is advanceable over the guide member, out of the distal end portion of the cannula and over the substantially continuous loop defined by the guide member
in which the cannula includes a first lumen and a second lumen, wherein the substantially continuous loop defined by the guide member extends from the first lumen and returns into the second lumen.

14. The system of claim 13 in which the at least one tissue manipulator is advanceable out of the first lumen over the substantially continuous loop defined by the guide member and returnable into the second lumen.

15. The system of claim 13 in which the second lumen has a larger cross-sectional profile than the first lumen.

16. The system of claim 13 further including a drive mechanism for advancing the at least one tissue manipulator along the guide member.

17. The system of claim 16 wherein the drive mechanism includes at least one pair of pinch rollers.

18. A method of manipulating tissue in or adjacent to an intervertebral disc space, comprising:
inserting a guide member into an intervertebral disc space;
forming a portion of the guide member into a substantially continuous looped configuration wherein the portion of the guide member extends into and returns out of the intervertebral disc space; and
advancing at least one tissue manipulator having a leading end and a trailing end along the portion of the guide member formed into the substantially continuous looped configuration to manipulate tissue within and/or adjacent to the disc space such that both the leading and trailing ends of the at least one tissue manipulator are advanced over the guide member first into and returning again from the intervertebral disc space, wherein the tissue manipulator comprises one or more of a blade including a cutting edge for cutting tissue, a tissue scraper including a scraping edge for scraping tissue and/or a tissue extractor including a tissue capturing structure for capturing and removing tissue from the intervertebral disc space.

19. The method of claim 18 wherein inserting the guide member into the intervertebral disc space comprises advancing the guide member through a cannula.

20. The method of claim 18, wherein advancing at least one tissue manipulator comprises advancing both the leading and trailing ends of the at least one tissue manipulator over the guide member from a first lumen into the intervertebral disc space and returning into a second lumen from the intervertebral disc space.

21. A tissue manipulation system for manipulating tissue in or adjacent to an intervertebral disc space, the system comprising:
an elongated guide member including a distal end portion adapted for insertion into an intervertebral disc space, the distal end portion of the guide member forming a substantially continuous looped configuration wherein the guide member extends into and returns out of the intervertebral disc space when positioned within the intervertebral disc space; and
at least one tissue manipulator having a leading end and a trailing end and comprising one or more of a blade including a cutting edge for cutting tissue, a tissue scraper including a scraping edge for scraping tissue and/or a tissue extractor including a tissue capturing structure for capturing and removing tissue from the intervertebral disc space, the at least one tissue manipulator having a passageway for receiving the guide member such that both the leading and the trailing ends of the at least one tissue manipulator are advanceable around the substantially looped configuration of the distal end portion of the guide member and first into and returning again from the intervertebral disc space.

22. The system of claim 21 in which the at least one tissue manipulator is adapted to disrupt disc tissue.

23. The system of claim 21 in which the at least one tissue manipulator is adapted to disrupt vertebral endplates.

24. The system of claim 21 in which the at least one tissue manipulator has a first portion adapted to disrupt disc tissue and a second portion adapted to disrupt vertebral endplates.

25. The system of claim 21 in which the at least one tissue manipulator comprises an elongated tubular element including a proximal end section defining the trailing end of the manipulator, a distal end section defining the leading end of the manipulator and a mid-section therebetween, wherein one or more tissue disruption elements are associated with the mid-section.

26. The system of claim 21 in which the at least one tissue manipulator is adapted to capture and remove tissue from the intervertebral disc space.

27. The system of claim 21 in which the at least one tissue manipulator includes a first tissue manipulator adapted to disrupt disc tissue, a second tissue manipulator adapted to disrupt vertebral endplates and a third tissue manipulator adapted to capture and remove tissue from the intervertebral disc space.

28. The system of claim 21 in which the at least one tissue manipulator is adapted to disrupt disc tissue, disrupt vertebral endplates and capture and remove tissue from the intervertebral disc space.

* * * * *